US007514256B2

(12) United States Patent
Barbera-Guillem

(10) Patent No.: US 7,514,256 B2
(45) Date of Patent: Apr. 7, 2009

(54) BIOREACTOR FOR SELECTIVELY CONTROLLING THE MOLECULAR DIFFUSION BETWEEN FLUIDS

(76) Inventor: Emilio Barbera-Guillem, 1555 Picardae Ct., Powell, OH (US) 43065

( * ) Notice: Subject to any disclaimer, the term of this patent is extended or adjusted under 35 U.S.C. 154(b) by 663 days.

(21) Appl. No.: 11/056,725

(22) Filed: Feb. 11, 2005

(65) Prior Publication Data
US 2006/0180529 A1 Aug. 17, 2006

(51) Int. Cl.
*C12M 3/00* (2006.01)
(52) U.S. Cl. .................. 435/293.1; 210/120; 210/436; 210/150; 210/206; 435/286.6; 435/289.1; 435/294.1
(58) Field of Classification Search .............. 435/286.6, 435/293.1, 294.1; 422/82
See application file for complete search history.

(56) References Cited

U.S. PATENT DOCUMENTS

| | | | |
|---|---|---|---|
| 3,732,149 A | 5/1973 | Santero | |
| 3,827,943 A | 8/1974 | Mann | |
| 3,853,712 A | 12/1974 | House et al. | |
| 3,948,732 A | 4/1976 | Haddad et al. | |
| D243,705 S | 3/1977 | Lyman | |
| 4,012,288 A | 3/1977 | Lyman et al. | |
| 4,178,209 A | 12/1979 | Tolbert et al. | |
| 4,184,916 A | 1/1980 | Tolbert et al. | |
| 4,208,483 A | 6/1980 | Lee | |
| 4,220,725 A | 9/1980 | Knazek et al. | |
| 4,241,187 A | 12/1980 | White | |
| 4,242,459 A | 12/1980 | Chick et al. | |
| 4,242,460 A | 12/1980 | Chick et al. | |

(Continued)

FOREIGN PATENT DOCUMENTS

EP 0878539 A2 11/1998

(Continued)

OTHER PUBLICATIONS

Nikaido, Hiroshi, Prevention of Drug Access to Bacterial Targets: Permeability Barriers and Active Flux, Science Apr. 15, 1994, vol. 264.

(Continued)

*Primary Examiner*—William H Beisner
*Assistant Examiner*—Michael Hobbs
(74) *Attorney, Agent, or Firm*—Michael J. Gallagher; David J. Dawsey; Gallagher & Dawsey Co., LPA

(57) ABSTRACT

A diffusion controlling bioreactor that selectively controls the molecular diffusion between fluids through a microchannel in fluid communication with a reaction reservoir. The length and cross-sectional area are selected to obtain a predetermined rate of molecular diffusion between fluids. When the fluids are liquids, flow through the microchannel is laminar and the capillary action of the microchannel and fluid is such that the fluid does not flow into the reaction reservoir unless the pressure of the fluid is increased by an external source, thereby minimizing contamination of the bioreactor. The instant invention may also utilize at least one microchannel and reagent reservoir to regulate, rather than prevent, the passage of various molecules into the bioreactor. A pressure equalizing vent operating on similar principles to the microchannel may have a structure configured to minimize the chances of fluid leakage from the bioreactor, even if the bioreactor is turned in various directions.

32 Claims, 21 Drawing Sheets

U.S. PATENT DOCUMENTS

| | | | |
|---|---|---|---|
| 4,296,205 A | | 10/1981 | Verma |
| 4,317,886 A | | 3/1982 | Johnson et al. |
| 4,321,330 A | | 3/1982 | Baker et al. |
| 4,349,632 A | | 9/1982 | Lyman et al. |
| 4,377,639 A | | 3/1983 | Lee |
| 4,391,912 A | | 7/1983 | Yoshida et al. |
| 4,426,451 A | * | 1/1984 | Columbus .................. 436/518 |
| 4,435,508 A | | 3/1984 | Gabridge |
| 4,495,289 A | | 1/1985 | Lyman et al. |
| 4,514,499 A | | 4/1985 | Noll |
| 4,537,860 A | | 8/1985 | Tolbert et al. |
| 4,546,083 A | | 10/1985 | Meyers et al. |
| 4,639,422 A | | 1/1987 | Geimer et al. |
| 4,657,867 A | | 4/1987 | Guhl et al. |
| 4,661,458 A | | 4/1987 | Berry et al. |
| 4,670,398 A | | 6/1987 | Song |
| 4,676,274 A | * | 6/1987 | Brown ........................ 137/806 |
| 4,680,266 A | | 7/1987 | Tschopp et al. |
| 4,995,974 A | * | 2/1991 | Lorey et al. ................ 210/247 |
| 5,010,013 A | | 4/1991 | Serkes et al. |
| 5,026,650 A | | 6/1991 | Schwarz et al. |
| 5,079,168 A | | 1/1992 | Amiot |
| 5,166,067 A | | 11/1992 | Ishida et al. |
| 5,240,854 A | | 8/1993 | Berry et al. |
| 5,254,471 A | | 10/1993 | Mori et al. |
| 5,256,570 A | | 10/1993 | Clyde |
| 5,272,084 A | | 12/1993 | O'Connell et al. |
| 5,283,187 A | | 2/1994 | Aebisher et al. |
| 5,290,700 A | | 3/1994 | Binot et al. |
| 5,398,837 A | | 3/1995 | Degrassi |
| 5,416,022 A | | 5/1995 | Amiot |
| 5,443,985 A | | 8/1995 | Lu et al. |
| 5,523,236 A | | 6/1996 | Nuzzo |
| 5,554,536 A | * | 9/1996 | Rising ..................... 435/305.1 |
| 5,587,128 A | * | 12/1996 | Wilding et al. ................ 422/50 |
| 5,622,857 A | | 4/1997 | Goffe |
| 5,639,423 A | * | 6/1997 | Northrup et al. ............. 422/50 |
| 5,672,507 A | | 9/1997 | Merk |
| 5,686,301 A | | 11/1997 | Falkenberg et al. |
| 5,686,304 A | | 11/1997 | Codner |
| 5,702,945 A | | 12/1997 | Nagels et al. |
| 5,707,869 A | | 1/1998 | Wolf et al. |
| 5,710,043 A | | 1/1998 | Pay |
| 5,736,399 A | | 4/1998 | Takezawa et al. |
| 5,785,964 A | | 7/1998 | Naughton et al. |
| 5,800,785 A | * | 9/1998 | Bochner .................... 422/101 |
| 5,801,054 A | | 9/1998 | Kiel et al. |
| 5,858,721 A | | 1/1999 | Naughton et al. |
| 5,863,792 A | | 1/1999 | Tyndorf et al. |
| 5,928,936 A | | 7/1999 | Ingram |
| 5,932,100 A | * | 8/1999 | Yager et al. ................ 210/634 |
| 5,958,762 A | | 9/1999 | Stoppini et al. |
| 5,972,369 A | | 10/1999 | Roorda et al. |
| 6,001,643 A | | 12/1999 | Spaulding |
| 6,010,633 A | * | 1/2000 | Zuk et al. .................. 210/767 |
| 6,037,171 A | | 3/2000 | Larsson |
| 6,043,079 A | | 3/2000 | Leighton |
| 6,114,165 A | | 9/2000 | Cai et al. |
| 6,150,159 A | | 11/2000 | Fry |
| 6,228,636 B1 | | 5/2001 | Yahiro et al. |
| 6,271,027 B1 | | 8/2001 | Sarem et al. |
| 6,284,451 B1 | | 9/2001 | FUnatsu et al. |
| 6,293,162 B1 | | 9/2001 | Mathur et al. |
| 6,303,375 B1 | | 10/2001 | Kimura et al. |
| 6,312,952 B1 | | 11/2001 | Hicks, Jr. |
| 6,329,195 B1 | | 12/2001 | Pfaller |
| 6,334,968 B1 | | 1/2002 | Shapiro et al. |
| 6,455,310 B1 | | 9/2002 | Barbera-Guillem |
| 6,811,968 B2 | | 11/2004 | Kirk et al. |
| 2002/0052049 A1 | * | 5/2002 | Weigl et al. ................. 436/180 |
| 2002/0058329 A1 | * | 5/2002 | Singh et al. .............. 435/287.2 |
| 2002/0072113 A1 | | 6/2002 | Barbera-Guillem |
| 2002/0076350 A1 | * | 6/2002 | Weigl et al. .................... 422/58 |
| 2002/0172621 A1 | * | 11/2002 | Barbera-Guillem ......... 422/100 |
| 2002/0187564 A1 | * | 12/2002 | Chow et al. ................. 436/518 |
| 2003/0064507 A1 | * | 4/2003 | Gallagher et al. ........ 435/287.2 |
| 2004/0005699 A1 | | 1/2004 | Roos et al. |
| 2004/0029266 A1 | | 2/2004 | Barbera-Guillem |
| 2004/0112751 A1 | * | 6/2004 | Han et al. .................... 204/605 |

FOREIGN PATENT DOCUMENTS

| | | |
|---|---|---|
| WO | WO 02/38460 A1 | 5/2002 |
| WO | WO 02/41969 A1 | 5/2002 |
| WO | WO 02/42419 A1 | 5/2002 |
| WO | WO 02/42421 A1 | 5/2002 |

OTHER PUBLICATIONS

Liu/Papadopoulos, Unidirectional Motility of *Escherichia coli* in Restrictive Cpillaries, Applied and Environmental Microbiology Oct. 1995, vol. 61.

Eisenbach, Michael, Bacterial Chemotaxis, Encyclopedia of Life Sciences 2001.

Shioi/Dang/Taylor, Oxygen As Attractant and Repellent in Bacterial Chemotaxis, Journal of Bacteriology Jul. 1987, vol. 169/No. 7.

Satnoianu/Maini/Garduno/Armitage, Travelling Waves in a Nonlinear Degerate Diffusion Model, Discrete and Continuous Dynamical Systems Aug. 2001, vol. 1/No. 3.

Hoyle/'Alcantara/Costerton, *Pseudomonas aeruginosa* Biofilm as a Diffusion Barrier to Piperacillin, Antimicrobial Agents and Chemotherapy Sep. 1992.

Lewus/Ford, Temperature-Sensitive Motility of *SUlfolobus acidocaldarius* Influences Population Distribution in Extreme Environments, Journal of Bacteriology Jul. 1999, vol. 181.

Bauwens/Yin/Dang/Peerani/Zandstra, Development of a Perfusion Fed Bioreactor for Embryonic Stem Cell-Derived Cardiomyocyte Generation, Wiley InterScience Mar. 18, 2005.

Watson/Watson/Warnes/Walker/Armstrong/Seamark, Preimplantation Development of In Vitro-Matured and In Vitro-Fertilized Ovine Zygotes, Biology of Reproduction 1994.

Dumoulin/Meijers/Bras/Coonen/Geraedts/Evers, Effect of Oxygen Concentration on Human in-vitro Fertilization and Embryo Culture, Human Reproduction 1999, vol. 14/No. 2.

Rancourt/Keng/Helt/O'Reilly, The Role of p21 in Growth of Epithelial Cells Exposed to Hyperoxia, Am J Physiol Lung Cell Mol Physiol 2001.

Fujitani/Kasai/Ohtani/Nishimura/Yamada/Utsumi, Effect of Oxygen Concentration and Free Radicals on In Vitro Development of In Vitro-Produced Bovine Embryos, J. Anim. Sci. 1997.

Pool, Thomas B., Recent Advances in the Production of Viable Human Embryos in vitro, Reproductive BioMEdicine Online Feb. 11, 2002, vol. 4/No. 3.

International Search Report and Written Opinion of the International Searching Authority for International Application No. PCT/US06/04578, mailed Apr. 8, 2008, 5 pages.

* cited by examiner

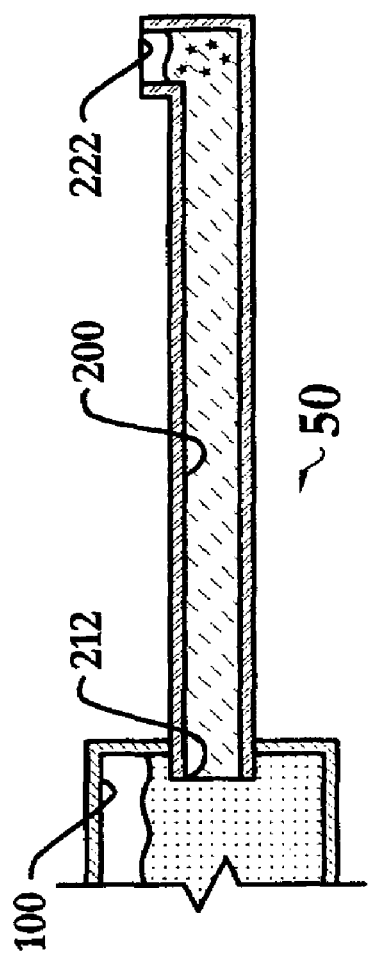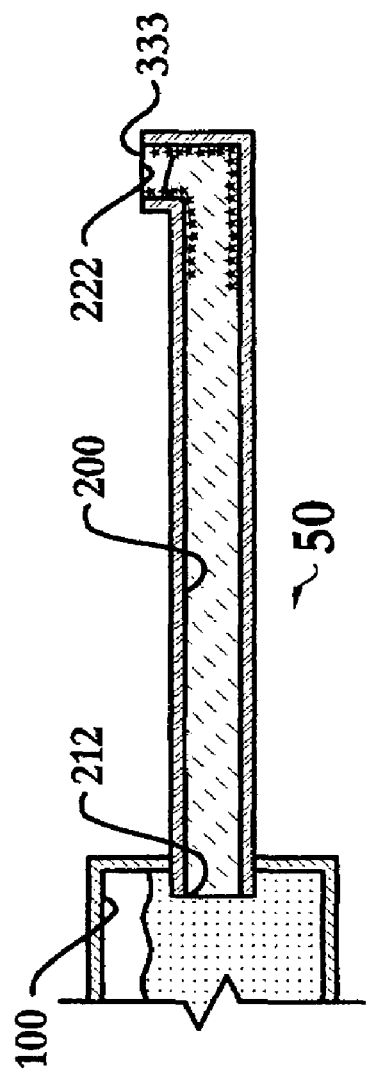

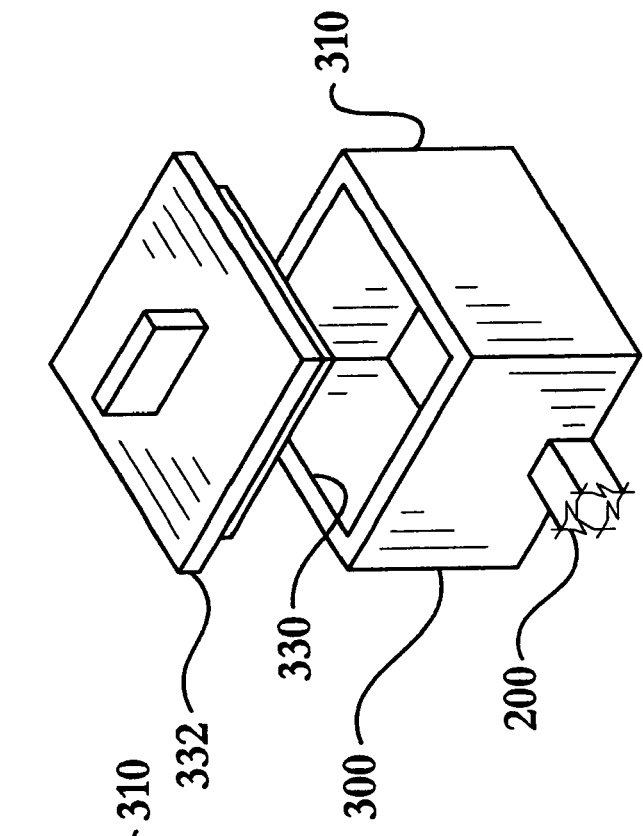
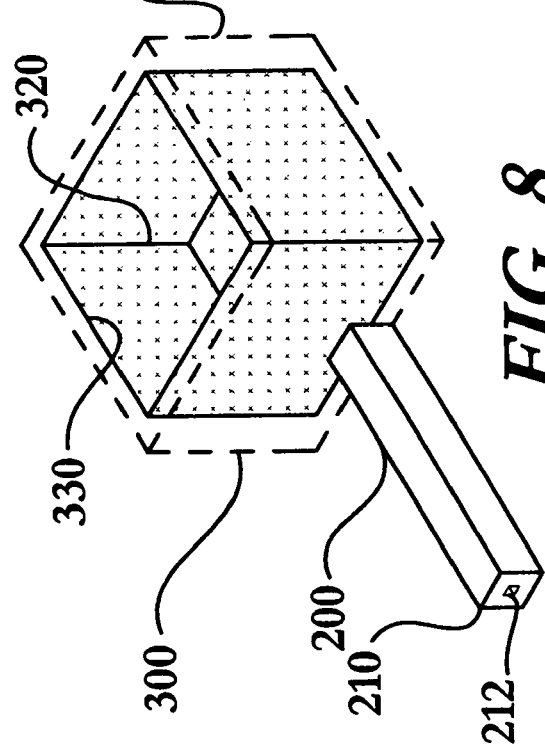
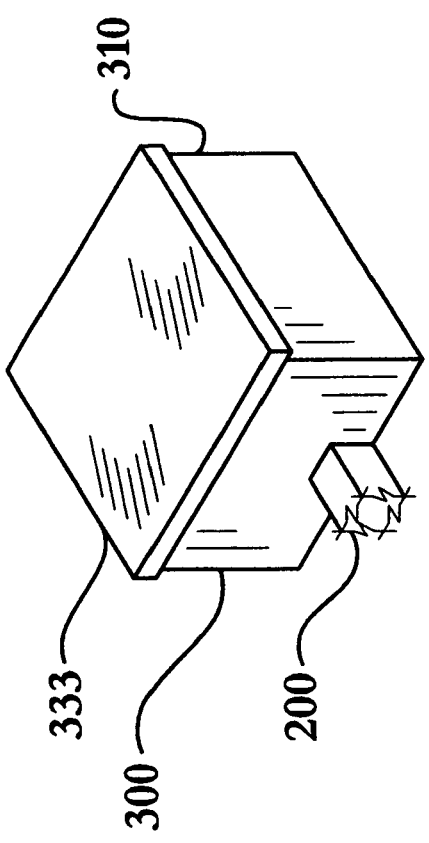
FIG. 8
FIG. 9
FIG. 10

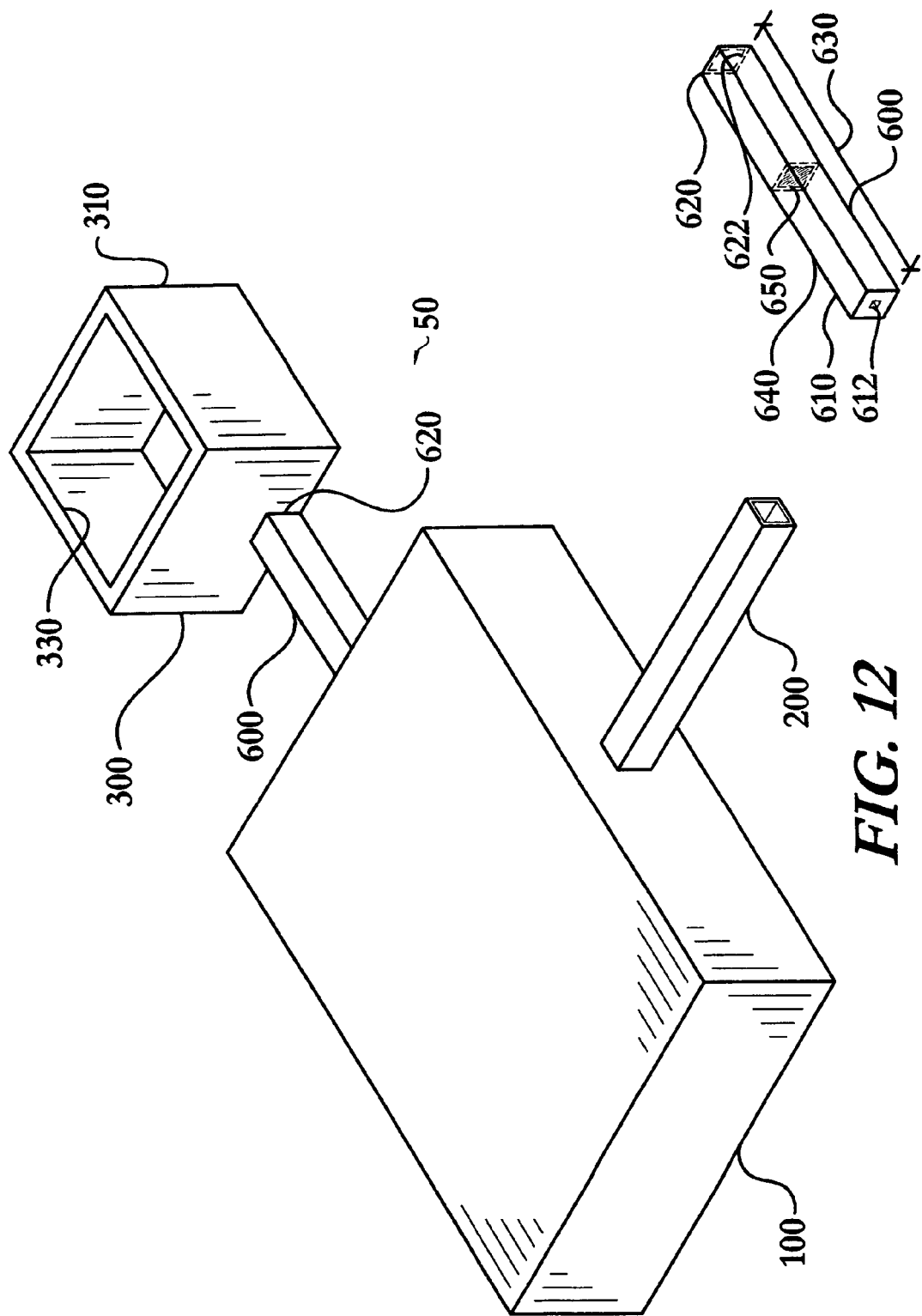

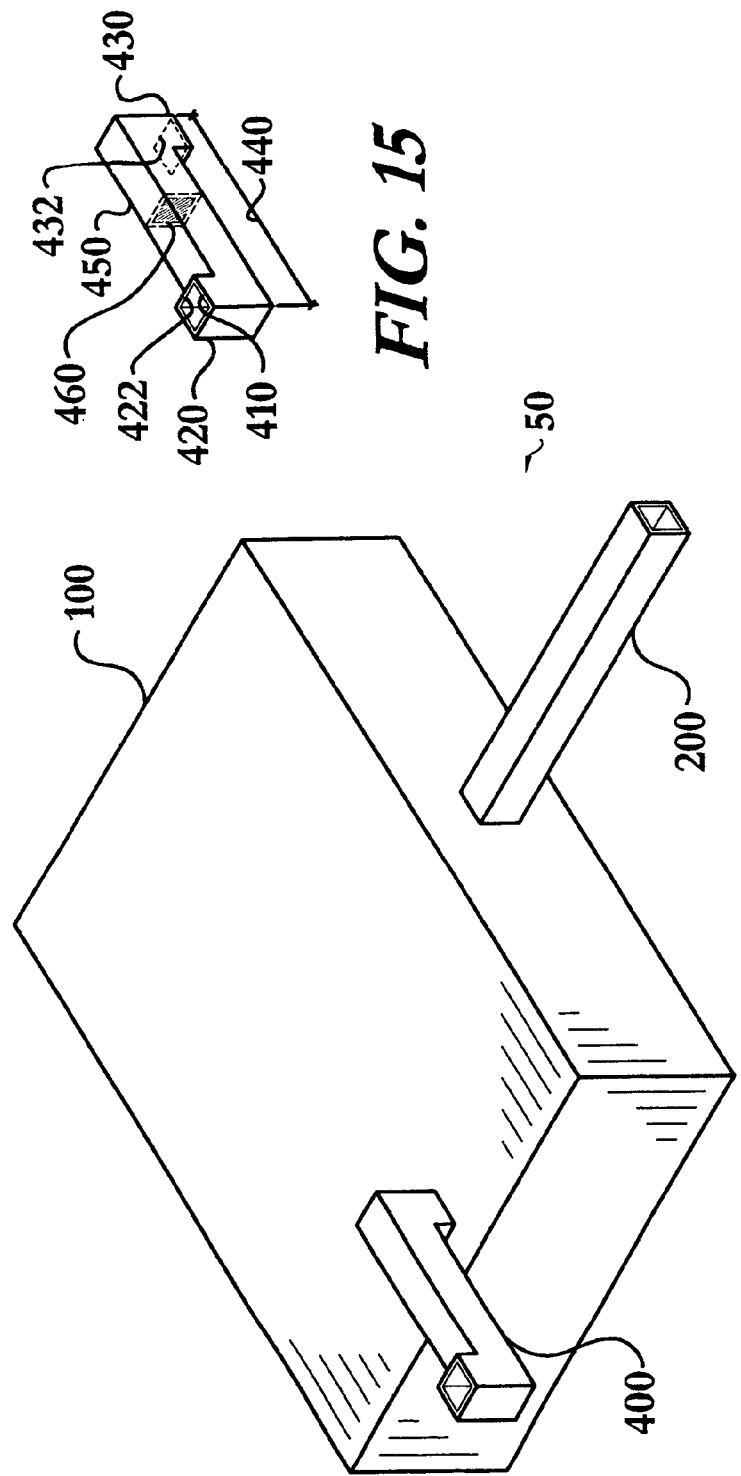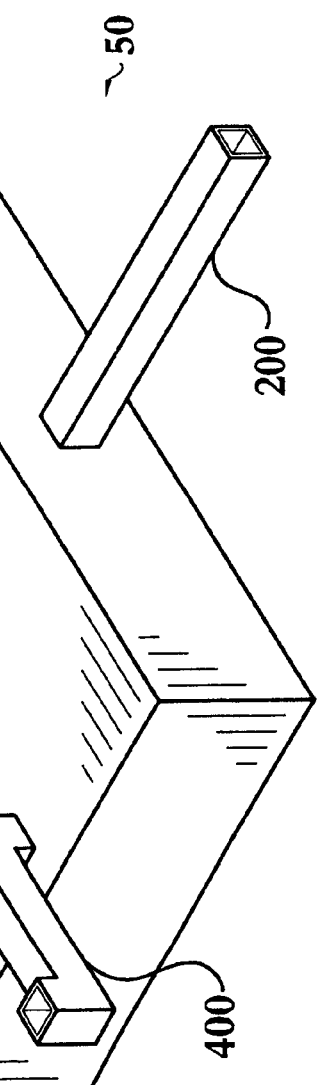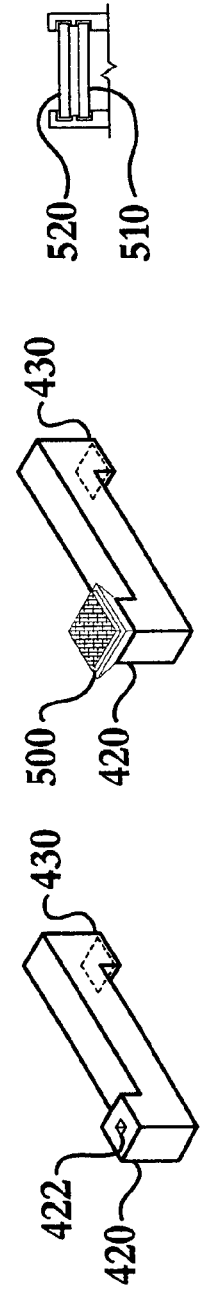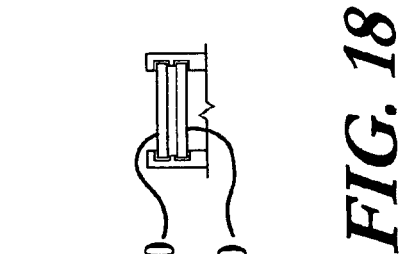

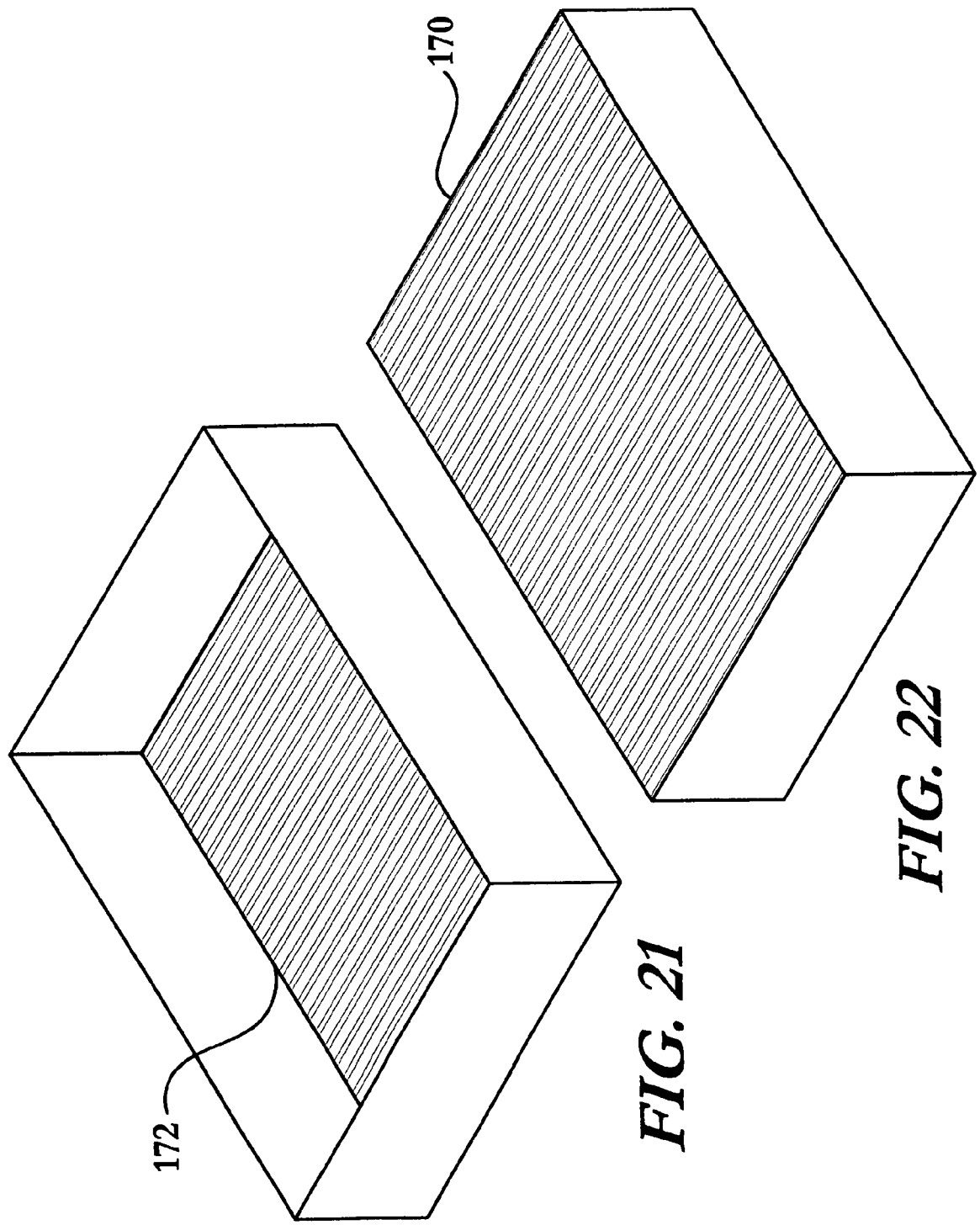

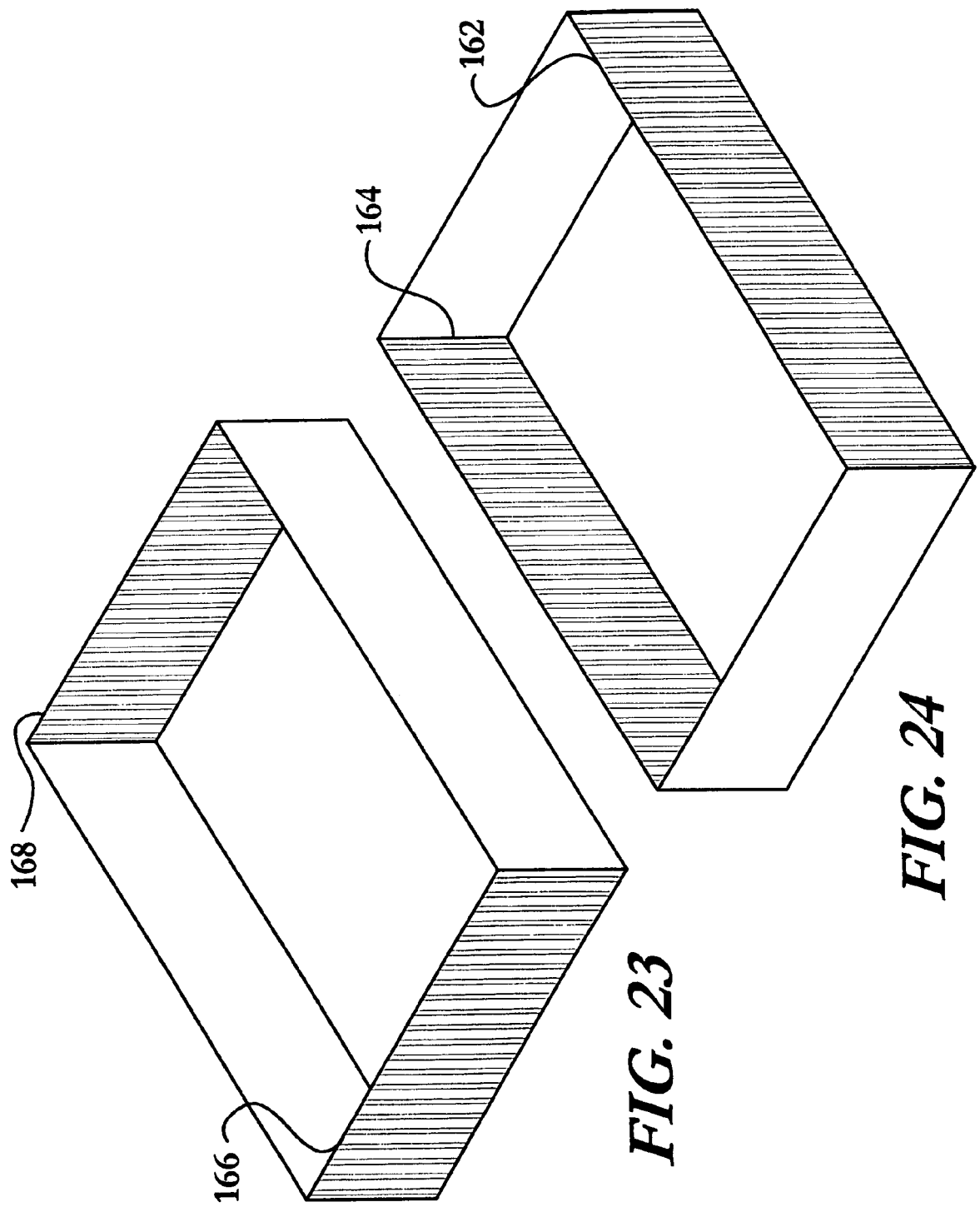

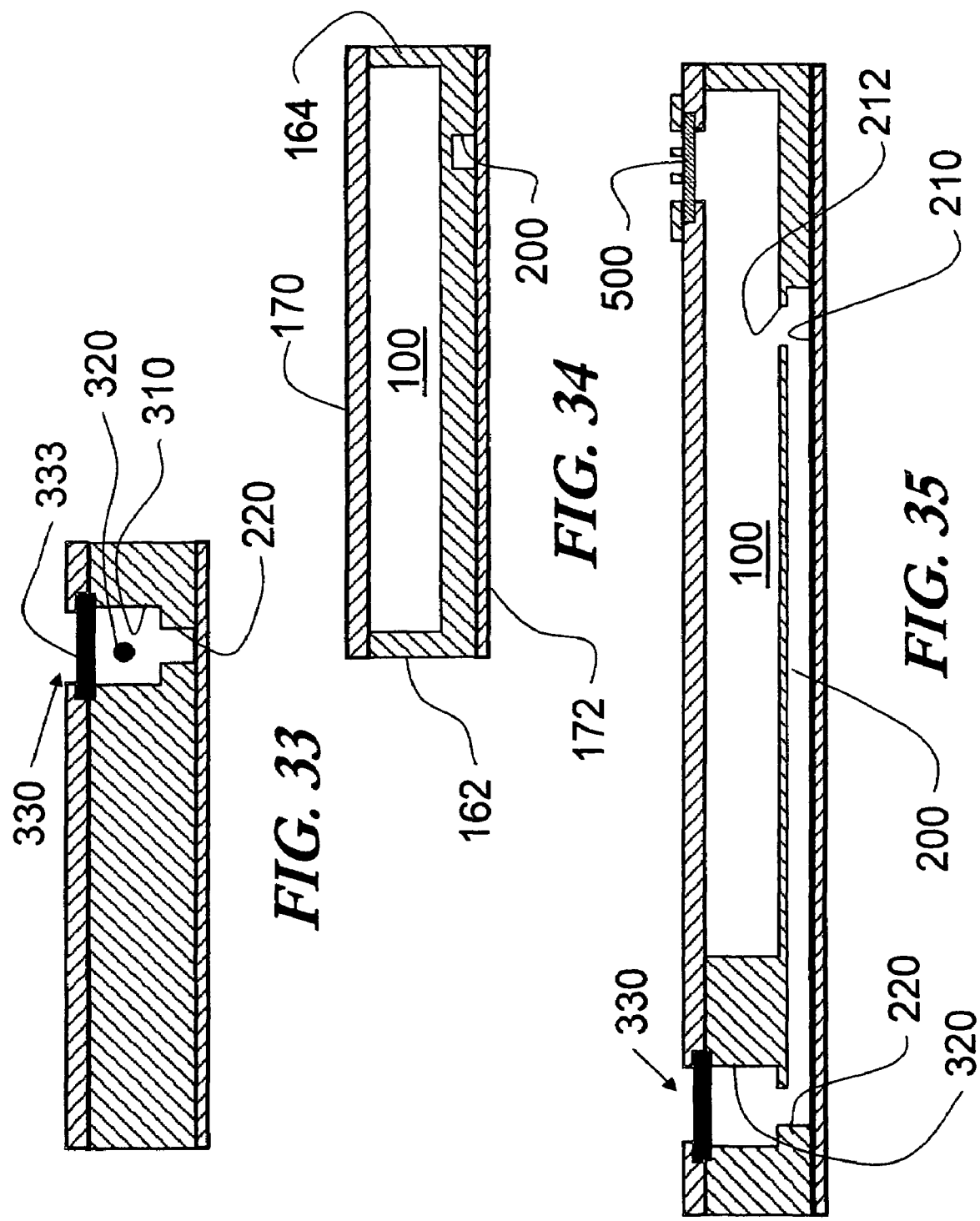

BIOREACTOR FOR SELECTIVELY CONTROLLING THE MOLECULAR DIFFUSION BETWEEN FLUIDS

TECHNICAL FIELD

The instant invention relates to a bioreactor for selectively controlling the molecular diffusion between fluids, particularly, to a bioreactor capable of very slow transfers of molecules into and out of the bioreactor by utilizing the Brownian motion of the molecules in given fluids.

BACKGROUND OF THE INVENTION

Bioreactors are common laboratory and industrial installations used in the areas of cell culture, chemical production, fermentation, testing and analysis, and other biological processes well known to those skilled in the art. A problem inherent in such bioreactors is the need to control the ingress and egress of various compounds to and from the bioreactor. As the size and volume of bioreactors decrease, or as the need to control becomes increasingly exacting, problems occur in the need to precisely control, over a long period of time or in respect of very small quantities of certain compounds, the movement of molecules both into and out of the bioreactor.

Various means have been employed to control small flows of fluids, in a field generally called microfluidics. In general, the means have proposed mechanical devices that are designed to mechanically, but accurately, deliver very small amounts of a fluid through various microchannels to a delivery point. A typical example is seen in U.S. Pat. No. 6,810,713; in which rotors periodically squeeze the microchannels formed in an elastic polymeric substrate to propel small amounts of fluid towards a delivery point by their compressive effect on the microchannel. Another approach is seen in U.S. Pat. No. 6,797,187; in which an electromagnetic field is used to generate a flow of a fluid in a microchannel lined, at least in part, with silicon nitride. Yet another approach is seen in U.S. Pat. No. 6,743,636; wherein pneumatically driven Venturi pumps move fluid through a microchannel system.

These approaches, and others that form the present art, rely on the movement of fluid volumes, albeit small ones, in order to transfer the various components that may be present in such fluids. Therefore, they fall prey to a myriad of problems. As the scale of the device decreases, it becomes increasingly difficult for a mechanical, or even electro-mechanical, device to control the very slow movement of molecules. Even slight variations in the operation of the various pumping mechanisms will result in wide swings, in a relative sense, in the amount of fluids transferred. The instant invention, on the other hand, is novel in its approach to controlling the displacement of various molecules into and out of a bioreactor system by controlling the rate of diffusion at an interface between two fluids, while minimizing any actual mixing of the fluids themselves. Therefore, the delivery of various molecules is inherently stable and predictable, and simple variations in the structure of the bioreactor suffice to control this diffusion.

SUMMARY OF INVENTION

In its most general configuration, the present invention advances the state of the art with a variety of new capabilities and overcomes many of the shortcomings of prior devices in new and novel ways. In its most general sense, the present invention overcomes the shortcomings and limitations of the prior art in any of a number of generally effective configurations.

In one configuration, the present invention relates to a method of using principles of diffusion to control the transfer of molecules into and out of a bioreactor. Diffusion is a reflection of the fact that molecules, as they vibrate with random motion, called Brownian motion, in a gas or liquid, move toward an equilibrium state where all the molecules in the mixture are uniformly dispersed, and the concentration of any molecular species is the same everywhere.

The diffusion equation (Fick's second law), states that the rate of molecular diffusion is proportional to the second derivative of its concentration. This can be written:

$$\frac{\partial C}{\partial t} = D\frac{\partial^2 C}{\partial x^2}$$

wherein C is the concentration, t is the time, and x is the distance.

FIG. 1 illustrates a diffusion model for a diffusion gradient along a long axis x, with diffusion progressing in the direction of the arrows. In a laminar flow state, the concentration of the diffusing substance will be equal at all points on a given plane orthogonal to the direction of laminar flow, illustrated as a first plane J1 and a second plane J2. In summary, given a theoretical scheme for diffusion between two compartments separated by a distance (x), as seen in FIG. 1, the diffusion equation could be expressed as:

$$\frac{\partial C_B}{\partial t} = D_B \frac{\partial^2 C_B}{\partial x^2}$$

Thus; to reach a certain concentration at plane $J_2$, given a concentration at plane $J_1$ of $C_B$, as seen in FIG. 1, the following variables will determine the diffusion between the planes:
1) Distance between planes $J_1$ and $J_2$ (x).
2) Time (t); and
3) Diffusion coefficient of the molecule ($D_B$), which will be constant for a given molecule for each specific fluid viscosity and temperature.

Therefore, for a given system the combination of distance and time will determine the rate of passage of a molecule from a first location, such as a point on plane J1 to a second location, such as a point on plane J2. The magnitude of molecular diffusion will be a function of both distance and time, along with the interface's surface area, that is, the area available for diffusion. Consequently, it is possible to control time of passage from a first location to a second location of a certain amount of a given molecule by setting the other four variables: surface area of the interface, fluid viscosity, temperature, and distance between the locations.

Contemplation will show that since the rate of diffusion is inversely related to the square of the distance between the compartments (x), relatively small increases in distance will have a large effect in slowing the rate of diffusion; and relatively large increases in distance will have an extremely large effect in slowing the rate of diffusion. The calculation of the rate of diffusion in both time and distance is complex; as an application of Fick's second law of diffusion, which can be expressed as follow for long distances:

$$\frac{dC}{dx} = -\frac{C_s}{\sqrt{\pi Dt}} \exp\left\{\frac{-x^2}{4Dt}\right\}$$

where C=concentration of substance in question, t=the time of diffusion, x=distance, Cs=starting concentration, and D=coefficient of diffusion for the molecule in the fluid.

A fast estimate of the rate of diffusion can be realized from the simpler relation that the time, (t), for 37% of the molecules to diffuse over the given distance, x, can be simply calculated as:

$$t = x^{D/2}$$

The figure of 37% comes from the fact that the process is exponential, e (the base of natural logs)=2.7183, therefore 1/e=0.37, or 37%. This calculation is for the simplest solution for diffusion in one dimension away from a plane. Note that as observed above, the time required for diffusion of a given quantity increases with the square of the distance.

In order to visualize the important effect of distance (x) in determining the rate of diffusion for a given molecule and fluid, one may compare illustrative applications. In a system where the fluid is water, the diffusing molecules are oxygen, and the system is maintained at 37° C., as seen in Table 1; the time value for 37% oxygen diffusion across three different spaces is calculated, each reflecting a difference in diffusion distance (x). The applications are diffusion: (a) across lung epithelium (having an average thickness of $5 \times 10^{-7}$ m); (b) from the atmosphere to the cell layer in a typical laboratory T flask (where the cell layer is separated from the atmosphere by an average distance of 0.003 m); and (c) from the atmosphere to the fluid inside an innovative bioreactor in which the principles of the instant invention are utilized to create a nearly one meter separation between the external environment and the reservoir of fluid within the device.

TABLE 1

| | x (m) | Oxygen D | Time sec | Days |
|---|---|---|---|---|
| a | $5 \times 10^{-7}$ | $1.8 \times 10^{-9}$ | 0.000035 | 0.00 |
| b | 0.003 | $1.8 \times 10^{-9}$ | 1,250 | 0.01 |
| c | 0.98 | $1.8 \times 10^{-9}$ | 133,388,889 | 1543.85 | x = distance in meters, D = coefficient of diffusion in water

Therefore, it is evident that by increasing the distance between compartments, it is possible to greatly slow diffusion, to a point at which diffusion becomes so slow that, for practical purposes, it stops. Therefore, by manipulating the separation between compartments in a bioreactor, as by way of example and not limitation, extending a long tube between otherwise separated compartments, it is possible to delay diffusion. Manipulation of the length of the tubing will control the rate of diffusion, if other variables are held steady and the movement of fluid is prevented. Nearing the extreme upward limit of delay mentioned above, such a system, as seen in various embodiments of the instant invention, can serve to create a virtual hermetic seal through which, on a practical basis, diffusion times are so long that there is effectively no movement of particular molecules from one end of the seal to the other. In other words, if sufficient distance is created, diffusion becomes so slow that it may be disregarded.

In a preferred embodiment, the instant invention includes a diffusion controlling bioreactor that selectively controls the molecular diffusion between a first fluid and a second fluid. The diffusion controlling bioreactor includes a microchannel in fluid communication with a reaction reservoir. The length and cross-sectional area of the microchannel are selected to obtain a predetermined rate of molecular diffusion between the first fluid and the second fluid. The flow of fluid through the microchannel is laminar and the capillary action of the microchannel and the fluid is such that the fluid does not flow into the reaction reservoir unless the pressure of the fluid is increased by an external source, which may or may not include the effects of gravity on the fluids.

In one of the applications of the instant invention, a microchannel may be configured of such a length and cross-sectional area that, when the microchannel is used to connect the filling means of the bioreactor with the reaction reservoir, microorganisms that may inadvertently contaminate the filling means of the bioreactor are prevented from successfully traversing the microchannel. The laminar flow state of fluid in the microchannel and lack of fluid flow into the reaction reservoir results in non-motile organisms failing to reach the reaction reservoir in generally applicable time frames, and the slow diffusion of nutrients and oxygen from the reaction reservoir toward such organisms results in the death of these organisms before they can diffuse or extend by colony growth to the bioreactor.

In addition to the ability to virtually "seal" the bioreactor from contaminants, the instant invention may utilize at least one microchannel and reagent reservoir to effect and regulate, rather than prevent, the passage of various molecules into the reaction reservoir of the bioreactor. For instance, various substances such as drugs in varying concentrations, nutrients, or other agents, may be introduced into the reagent reservoir in the form of a first fluid, which is in fluid communication through the microchannel to the reaction reservoir, which contains a second fluid. The microchannel is sized to have a length and cross-sectional area that may predetermine a rate of diffusion for such substances into the reaction reservoir. The user fills the microchannel and the reagent reservoir only sufficiently to advance the first fluid to the proximal end of the microchannel. At that point, as long is there is a difference in viscosity between the first and second fluid, and unless the microchannel is pressurized above or below the pressure of the reaction reservoir, there will be no movement of fluid between the microchannel and the reaction reservoir, only diffusion of molecules at the interface between the fluids contained in each.

The bioreactor may further incorporate a pressure equalizing vent that operates on similar principles to the microchannel described above. The pressure equalizing vent may have a structure configured to minimize the chances of fluid leakage from the bioreactor, even if the bioreactor is turned in various directions.

BRIEF DESCRIPTION OF THE DRAWINGS

Without limiting the scope of the present invention as claimed below and referring now to the drawings and figures:

FIG. 5 shows a cross-section view of a microchannel of the bioreactor of FIG. 2, not to scale;

FIG. 6 shows a cross-section view of a microchannel of the bioreactor of FIG. 2, not to scale;

FIG. 8 shows a portion of the embodiment of the bioreactor of FIG. 7 in elevated perspective view, not to scale;

FIG. 9 shows a portion of another embodiment of the bioreactor of FIG. 7 in elevated perspective view, not to scale;

FIG. 10 shows a portion of another embodiment of the bioreactor of FIG. 7 in elevated perspective view, not to scale;

FIG. 12 shows another embodiment of the bioreactor of the instant invention in elevated perspective view, not to scale;

FIG. 13 shows a portion of the embodiment of the bioreactor of FIG. 12 in elevated perspective view, not to scale;

FIG. 14 shows another embodiment of the bioreactor according to the instant invention in elevated perspective view, not to scale;

FIG. 15 shows a portion of the embodiment of the bioreactor of FIG. 14 in elevated perspective view, not to scale;

FIG. 16 shows a portion of another embodiment of the bioreactor of FIG. 14 in elevated perspective view, not to scale;

FIG. 17 shows a portion of another embodiment of the bioreactor of FIG. 14 in elevated perspective view, not to scale;

FIG. 18 shows a portion of the embodiment of the bioreactor of FIG. 17 in elevated perspective view, not to scale;

FIG. 21 shows detail of a surface of the bioreactor of the instant invention in elevated perspective view, not to scale;

FIG. 22 shows detail of a surface of the bioreactor of the instant invention in elevated perspective view, not to scale;

FIG. 23 shows detail of two surfaces of the bioreactor of the instant invention in elevated perspective view, not to scale;

FIG. 24 shows detail of two surfaces of the bioreactor of the instant invention in elevated perspective view, not to scale;

FIG. 33 shows a cross-section view of the bioreactor of FIG. 32 viewed across section line A-A in FIG. 32, not to scale;

FIG. 34 shows a cross-section view of the bioreactor of FIG. 32 viewed across section line B-B 9 in FIG. 32, not to scale;

FIG. 35 shows a cross-section view of the bioreactor of FIG. 32 viewed across section line C-C in FIG. 32, not to scale;

DETAILED DESCRIPTION OF THE INVENTION

The method and materials of the bioreactor for selectively controlling the molecular diffusion between fluids of the instant invention enables a significant advance in the state of the art. The preferred embodiments of the method and materials accomplish this by new and novel arrangements of elements and methods that are configured in unique and novel ways and which demonstrate previously unavailable but preferred and desirable capabilities.

The detailed description set forth below in connection with the drawings is intended merely as a description of the presently preferred embodiments of the invention, and is not intended to represent the only form in which the present invention may be constructed or utilized. The description sets forth the designs, functions, means, and methods of implementing the invention in connection with the illustrated embodiments. It is to be understood, however, that the same or equivalent functions and features may be accomplished by different embodiments that are also intended to be encompassed within the spirit and scope of the invention.

Figure 1:
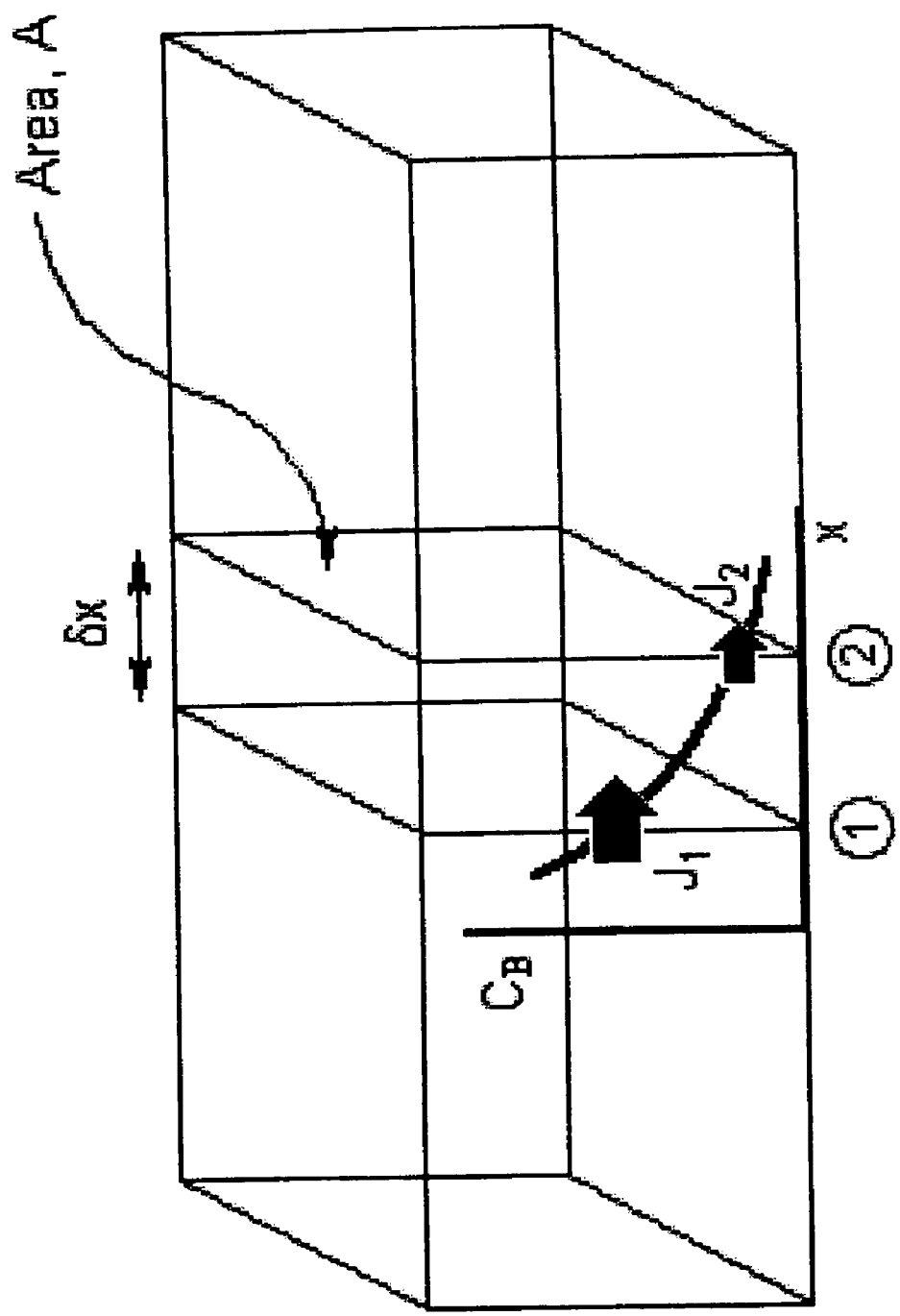
FIG. 1 shows a diffusion model illustrating a diffusion process in a laminar flow state proceeding in the direction of the arrows along the long axis of the model.
Figure 2:
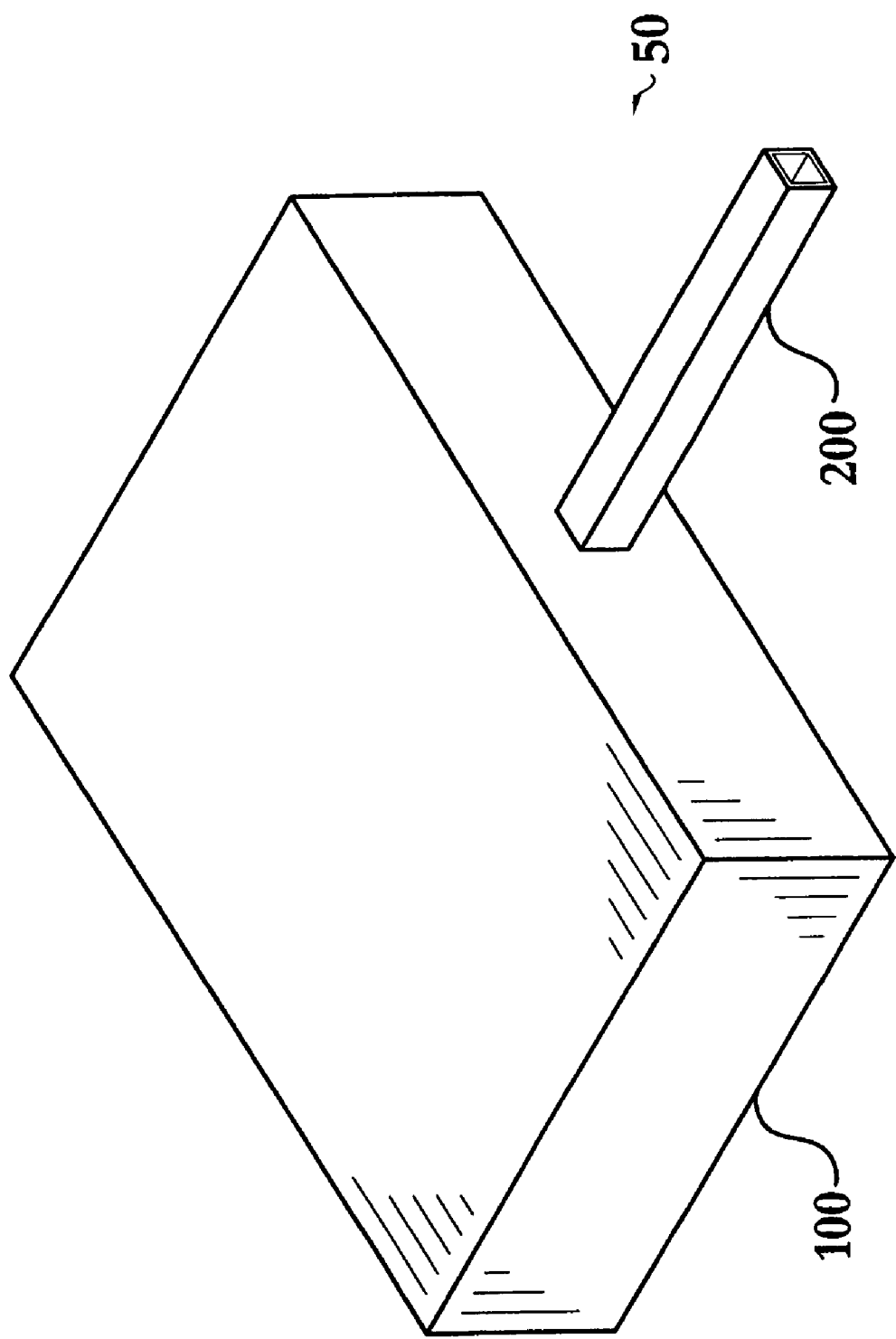
FIG. 2 shows an embodiment of a bioreactor according to the instant invention in elevated perspective view, not to scale.
Figure 3:
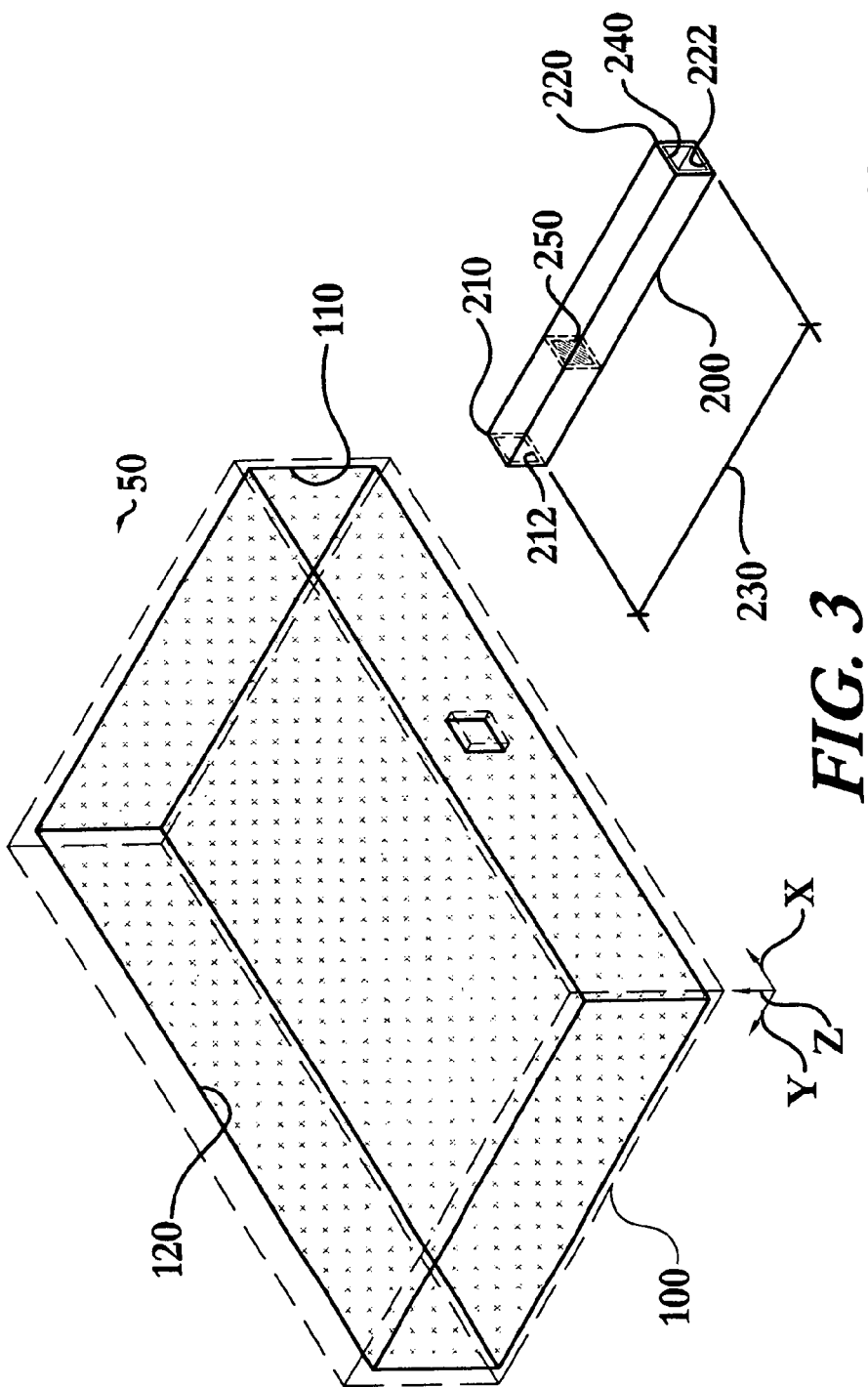
FIG. 3 shows detail of the embodiment of the bioreactor of FIG. 2 in elevated perspective view, not to scale, with the microchannel shown separated from the reaction reservoir for clarity.
Figure 4:
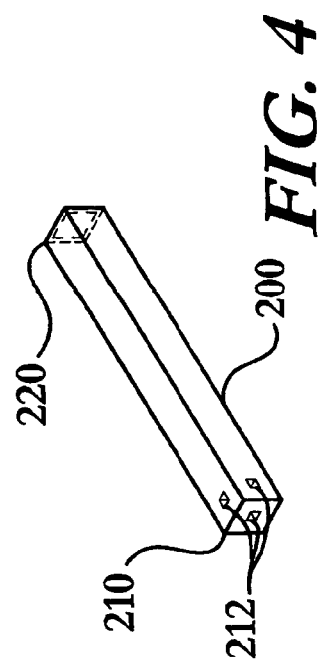
FIG. 4 shows a variation of the detail of the microchannel of the bioreactor of FIG. 2 in elevated perspective view, not to scale.

In a preferred embodiment, seen in FIGS. 2 through 4, the instant invention includes a diffusion controlling bioreactor 50 that selectively controls the molecular diffusion between a first fluid and a second fluid, and includes a reaction reservoir 100 having at least one reaction reservoir sidewall 110 that defines a reaction reservoir volume 120 and a microchannel 200. The reaction reservoir 100 initially contains the first fluid.

The microchannel 200 is in fluid communication with the reaction reservoir 100. As seen in FIG. 3, the microchannel 200 has a proximal end 210 with a proximal end opening 212, a distal end 220 with a distal end opening 222, a length 230, and at least one microchannel sidewall 240 having a sidewall thickness 245, and defining a cross-sectional area 250. The length 230 and cross-sectional area 250 are selected to obtain a predetermined rate of molecular diffusion between the first fluid in the reaction reservoir 100 and the second fluid in the microchannel 200. The microchannel 200 is configured in a manner such that when the microchannel 200 is filled with the second fluid, and the second fluid is a liquid, flow of the second fluid through the microchannel 200 is laminar. The capillary action of the microchannel 200 and the second fluid is such that the second fluid does not flow into the reaction reservoir 100 unless the pressure of the second fluid is increased by an external source, such as, by way of example and not limitation, pressurization of the microchannel caused by an increase of temperature.

Figure 27:
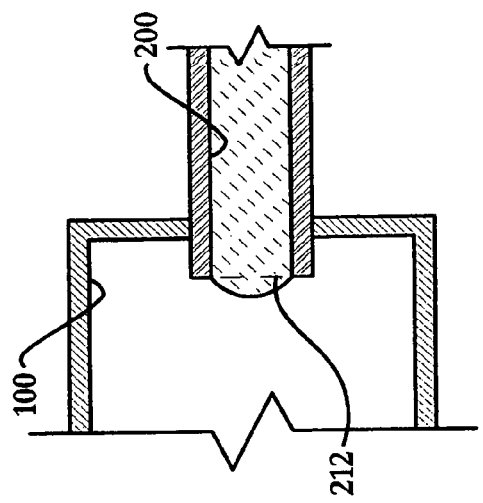
FIG. 27 shows a portion of an embodiment of the bioreactor of the instant invention in cross-sectional view, not to scale.
Figure 28:
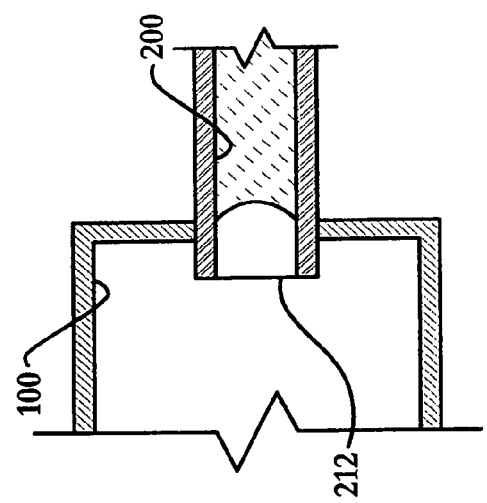
FIG. 28 shows a portion of an embodiment of the bioreactor of the instant invention in cross-sectional view, not to scale.

For example, assuming that the reaction reservoir 100 is initially empty, or only contains air, as a user fills the microchannel 200 through the microchannel distal end opening 222 with a second fluid that is a liquid, the capillary action of the microchannel 200 and the second fluid results in the second fluid being drawn to the microchannel proximal end 210, as seen in FIG. 27, until the liquid reaches the proximal end opening 212, as seen in FIG. 28, where it stops. This is also the situation when the reaction reservoir 100 contains a liquid and the liquid is not soluble with the liquid that is introduced and drawn from the microchannel distal end opening 222 to the microchannel proximal end opening 212.

One illustrative embodiment of the instant invention, seen in FIGS. 5 and 6, utilizes a predetermined rate of diffusion to act as an antiseptic barrier in a diffusion controlling bioreactor 50. Contamination is a consistent problem in the laboratory and commercial uses of most bioreactors, especially in eukaryotic cell cultures. Ports, most often made of penetrable elastomeric septa, are used to introduce and remove various components from bioreactors, most often by means of a pipette-like device that first punctures the septum, and then adds or removes components from the bioreactor. The septum is designed to resealably close after withdrawal of the pipette. It is well known in the art that such punctures tend to introduce contamination into the system, by either the pipette directly introducing bacteria through the punctured septum at the time of puncture, or by the pipette leaving a very small defect, or defects after repeated use, after withdrawal of the pipette. Organisms, for example, bacteria, yeast, and fungi, eventually migrate through these very small defects.

As applied to the instant invention, the introduced organisms, represented in FIG. 5 by small stars, would tend to mix with the fluid present in the distal end 220 of the microchannel 200. Small colonies of bacteria or yeast would tend to begin growth on the interior wall of the distal end 220, or in close proximity to the distal end opening 222, as see in FIG. 5. The microchannel 200 must be sized so that only laminar flow of fluid is possible when the fluid is a liquid. As is well-known in the art, by way of example and not limitation, a microchannel 200 with a cross-sectional area of less than approximately 4 $mm^2$ will satisfy this requirement for many liquids.

Once the microchannel 200 is filled with fluid, flow stops and the microchannel remains in a laminar flow state. Should flow resume, or currents develop within the fluid, due to, by way of illustration and not limitation, agitation or heating of the fluid, the sizing of the microchannel ensures that only laminar fluid movement can take place within the microchannel. Non-motile bacteria, due to the exclusively laminar flow characteristics of the microchannel 200, are limited in their movement through the fluid present in the microchannel 200 to diffusion through the fluid. The diffusion constant of non-flagellated bacteria, as is well known in the art, is between around 0.0000001 $cm^2$/sec and 0.0000017 $cm^2$/sec. As a result, for an illustrative embodiment utilizing a microchannel 200 of the instant invention that is 10 cm long, it will take between 1 and 21 years for most bacteria to diffuse from the distal end 220 of the microchannel 200 to the reaction reservoir 100.

Additionally, living contaminants such as bacteria, yeast and fungi can be transported by direct extension, or colony growth, represented as small stars along the interior walls of the microchannel 200 near the distal end opening 222, as seen in FIG. 6. Most common organisms, certain flagellated or other motile bacteria excepted, will grow confluently in all directions from their initial point of attachment, including along the microchannel 200 of the instant invention towards the reaction reservoir 100. The fluid in the microchannel 200 may contain necessary survival requirements for all microorganisms, such as sugars and amino acids. Furthermore, the fluid may contain oxygen, a necessary requirement for the existence and growth of aerobic life forms. These required substances, if consumed by bacterial growth at the distal end 220 of the microchannel 200 will diffuse through the fluid from the reaction reservoir 100 towards the distal end 220 of the microchannel 200 at a rate predetermined by the cross-sectional area 250 and length 230 of the microchannel 200. Additionally, such growth, along with the normal metabolic needs of the undesirable organisms, will necessarily begin consuming the required substances at the distal end opening 222 of the distal end 220 of the microchannel 200.

The eventual contamination of the reaction reservoir 100 by extending organism colonies becomes a race in time for the organisms to grow to the reaction reservoir 100 before consuming the oxygen and nutrients along the route of growth through the microchannel 200, or oxygen and nutrients that the organisms can obtain due to diffusion of the nutrients and oxygen towards the organisms. The consumption and exhaustion of oxygen and nutrients will lead to stoppage of organism growth, and therefore stoppage of the migration. It therefore becomes possible for one skilled in the art, knowing the diffusion constants of such common gases as oxygen and carbon dioxide, and such common nutrients as glucose and lipids, to configure a microchannel 200 of such length 230 and cross-sectional area 250 that the resultant diffusion times of various molecules may be easily calculated. In an illustrative embodiment, the aforementioned microchannel 200 with a length 230 of 10 cm will result in a diffusion time, by the equations given in the Background of the Invention above, along the length 230 of the microchannel 200 of 36.2 days for oxygen, 42.2 days for carbon dioxide, and 85.8 days for glucose, in a water based system maintained at 37° C. Even a microchannel 200 that is significantly shorter than the preceding example will have a significant effect on diffusion time. For example, a microchannel that is only 1 cm in length 230, will have diffusion times of 8.7 hours for oxygen, 10.2 hours for carbon dioxide, and 20.6 hours for glucose, in a water based system maintained at 37° C.

Accordingly, it is highly likely that any living contaminants will perish from lack of oxygen, acidosis due to failure of the removal of carbon dioxide from the peri-cellular environment, or deprivation of nutrients, long before they can reach the reaction reservoir 100 of the instant invention, given the usual range of times during which laboratory or commercial biological processes are conducted. Therefore, as seen in FIGS. 5 and 6, the microchannel 200 tends to act as an antimicrobial barrier to contamination of the bioreactor 50, even should contaminants pass any physical barriers, such as a cap 332, or a resealable elastomeric septum 333, as seen in FIGS. 9 and 10, that may be present at the distal end opening 222 of the microchannel 200. Thus, in such an embodiment, the controlled diffusion through the microchannel 200 is used to effect a virtual "seal" between the reaction reservoir 100 and an external environment.

Again as applied to the instant invention, such a virtual "seal" may be used to limit the diffusion of gases into and out of the bioreactor 50 to that which takes place across the walls of the bioreactor. By way of example and not limitation, certain cell cultures, such as stem cells, require a carefully regulated oxygen environment. Unrestricted access by oxygen to these cells can result in cell death or transformation. The bioreactor 50 may be designed with a predetermined surface area to the walls of the bioreactor 50, and be built of a material having a predetermined diffusion constant for oxygen. In this way, the bioreactor 50 may auto-regulate the amount of oxygen available for the biological process within. Therefore, in a cell culture or similar application, the bioreactor 50 may be configured in such a manner and from such a material that a surface area of the reaction reservoir 100 (formed by the surfaces 162, 164, 166, 168, 170, and 172) and the oxygen diffusion constant of the reaction reservoir sidewall 110 material, result in the diffusion of a predetermined amount of oxygen per unit of time, calculated to support the metabolic needs of a predetermined number of cells. By way of example and not limitation, in a cell culture application, the bioreactor 50 may be formulated of a plastic material and with a reaction reservoir surface area such that 4.6 ml of oxygen is diffused, to support the metabolic needs of approximately $2 \times 10^7$ cells, at atmospheric pressure and 37° C., per day.

In addition to the ability to virtually "seal" the bioreactor 50 from contaminants and gases, the instant invention may utilize at least one microchannel 200 and reagent reservoir 300 to promote and regulate, rather than prevent, the passage of various molecules into the reaction reservoir 100 of the bioreactor 50.

In another embodiment, as seen in FIGS. 7 through 11, there may be a reagent reservoir 300 at the distal end 220 of the microchannel 200 that is in fluid communication with both the microchannel 200 and the reaction reservoir 100. In such an embodiment, the reagent reservoir 300 has at least one reagent reservoir sidewall 310 defining a reagent reservoir volume 320, seen in FIG. 8, and has a reagent reservoir opening 330 through which the second fluid enters the reagent reservoir 300. The reagent reservoir opening 330 may be closed by a cap 332, or by a penetrable, self-sealing, elastomeric septum 333, among other methods, as seen in FIGS. 9 and 10.

Figure 11:
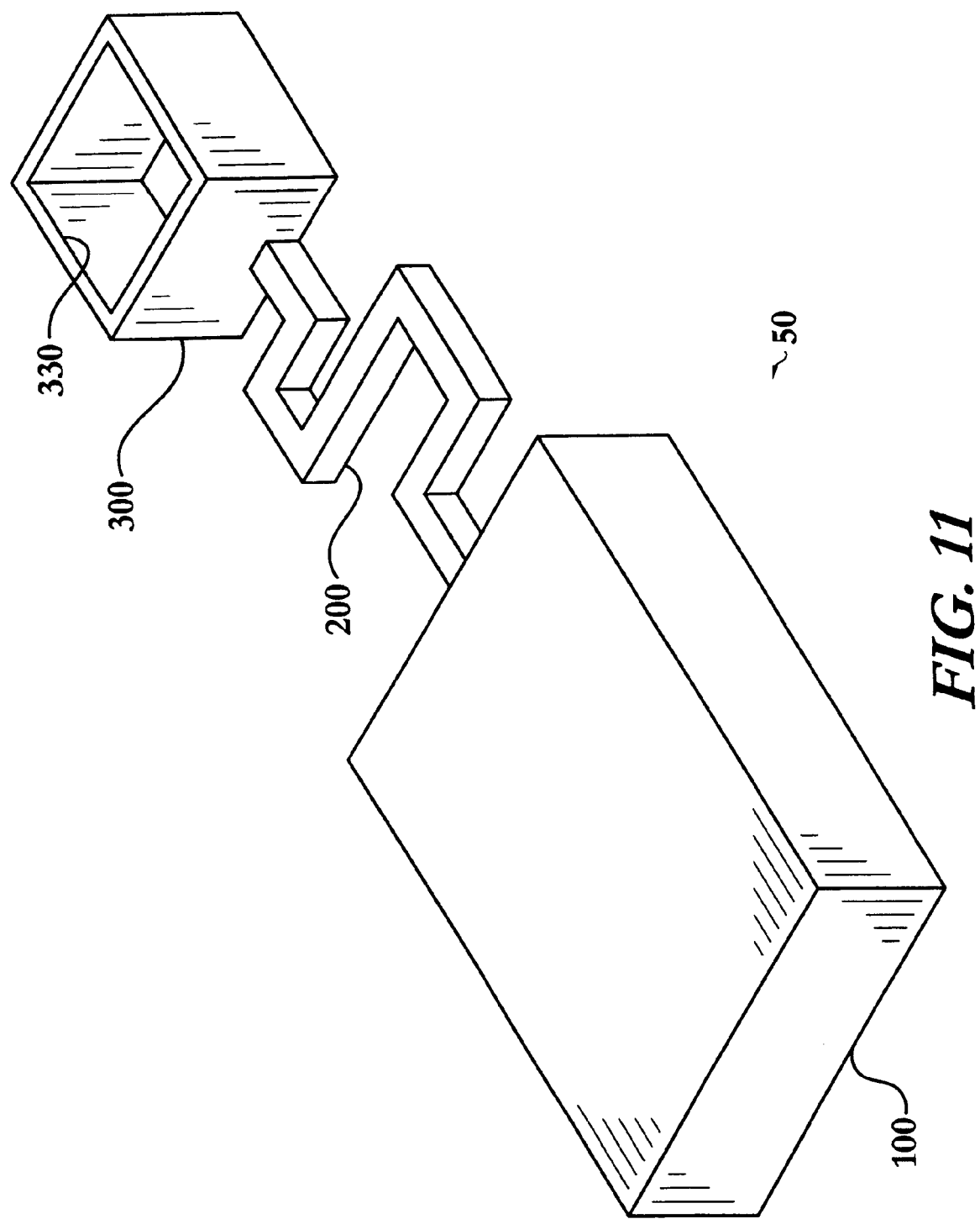
FIG. 11 shows another embodiment of the bioreactor of FIG. 7 in elevated perspective view, not to scale.
Figure 36:
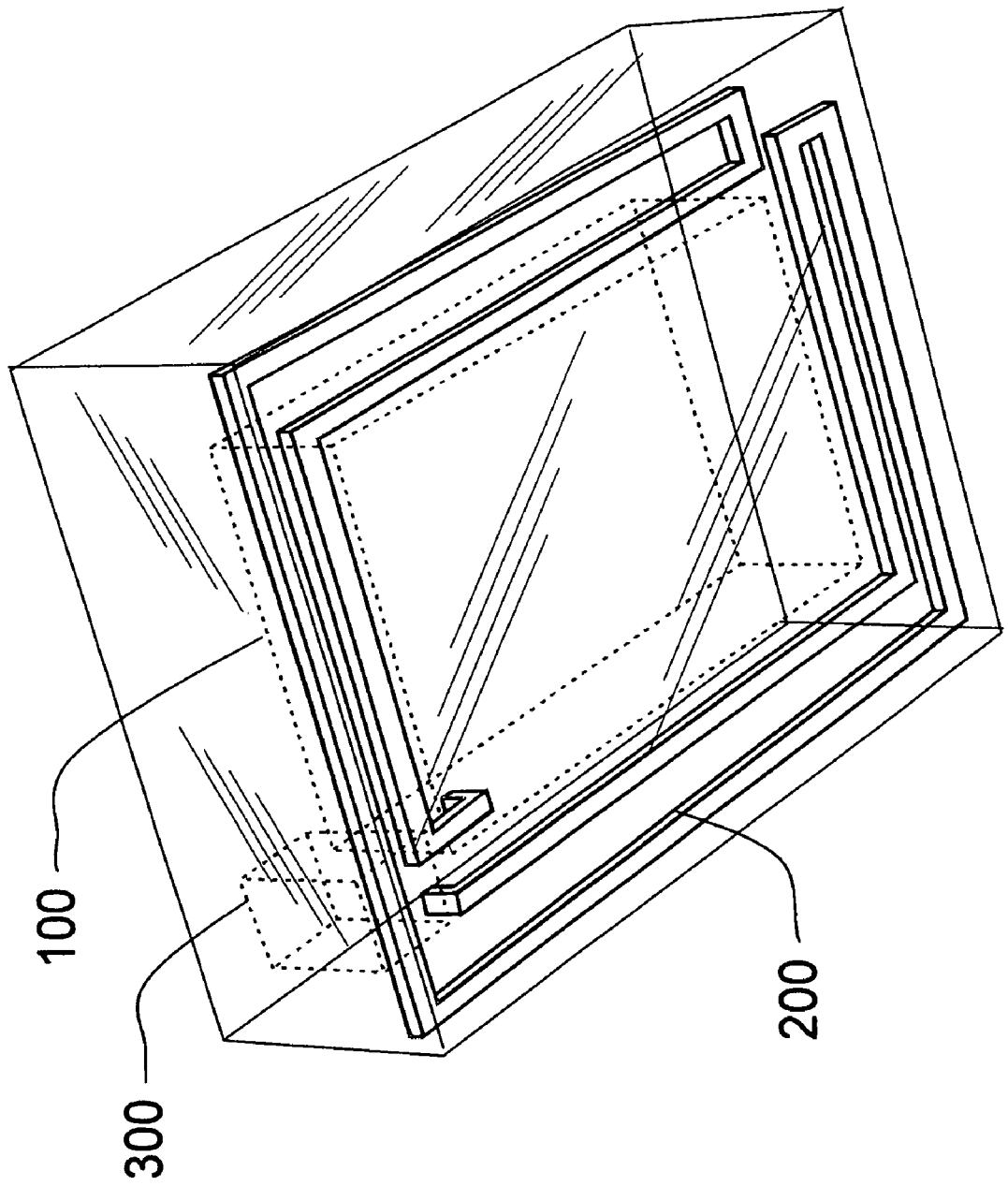
FIG. 36 shows another embodiment of the bioreactor of FIG. 7, in elevated perspective view, not to scale.

Various substances such as drugs in varying concentrations, nutrients, or other agents, may be introduced into the reagent reservoir 300, which is in fluid communication through the microchannel 200 to the reaction reservoir 100. The reagent reservoir 300 is designed to hold a reagent reservoir volume 320, and the microchannel 200 may be configured with a particular length 230 and cross-sectional area 250, as seen in the preceding embodiment illustrated in FIG. 3. Thus, the delivery by diffusion of a plurality of molecules into and out of the bioreactor 50 may be predetermined and easily effected. The length 230 and cross-sectional area 250 of the microchannel 200 is capable of wide variation, as would be known to one skilled in the art, as long as the basic requirement is met that the microchannel 200 be sized so that there is only laminar flow within the microchannel 200. In several embodiments, a cross-sectional area 250 of less than 4 mm² performs well. As would be appreciated by one skilled in the art, the rate of diffusion for a given substance, fluid, and temperature is determined by the length 230 and cross-sectional area 250 of the microchannel 200, and is entirely independent of the shape of the microchannel 200, and in particular is independent of any turns in the microchannel 200. Accordingly, and as seen in FIGS. 11 and 36, the microchannel may be configured in a wide array of shapes, including a variety of cross-sectional profiles such as the rectangular and circular profiles seen in the accompanying Figures, in order to accommodate various lengths 230, reagent reservoir volumes 320, and reaction reservoir volumes 120 and other design criteria.

During use, the user fills the microchannel 200, and the reagent reservoir 300 only sufficiently to advance the first fluid to the proximal end of the microchannel 200. At that point, as long is there is a difference in viscosity between the first and second fluid, and unless either the "interfacial tension" between the first fluid and the second is unbalanced in favor of the second, or the microchannel 200 is pressurized above or below the pressure of the reaction reservoir 100, there will be no movement of fluid between the microchannel 200 and the reaction reservoir 100, only diffusion at the interface between the fluids contained in each.

Figure 26:
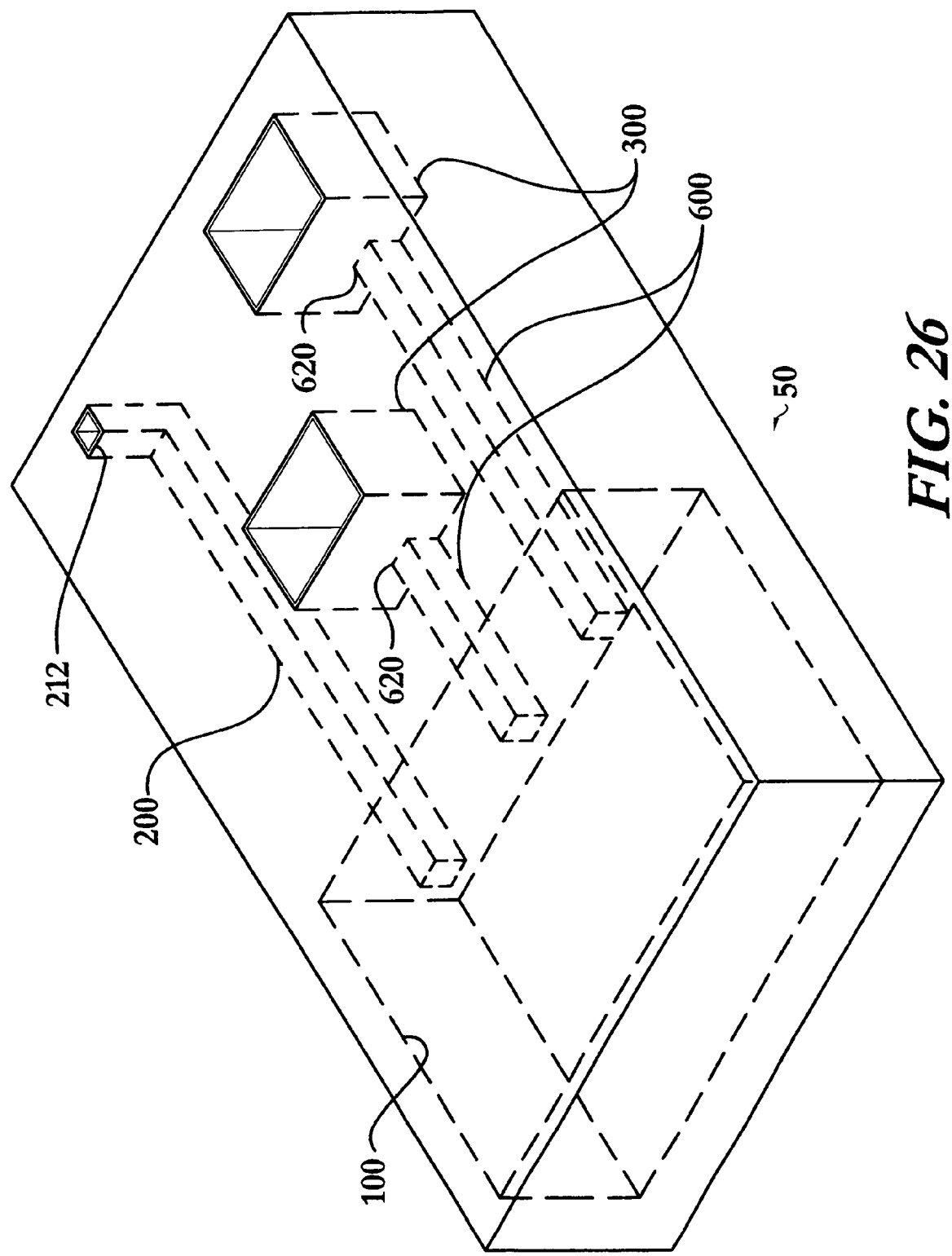
FIG. 26 shows another embodiment of the bioreactor of the instant invention in elevated perspective view, not to scale.
Figure 31:
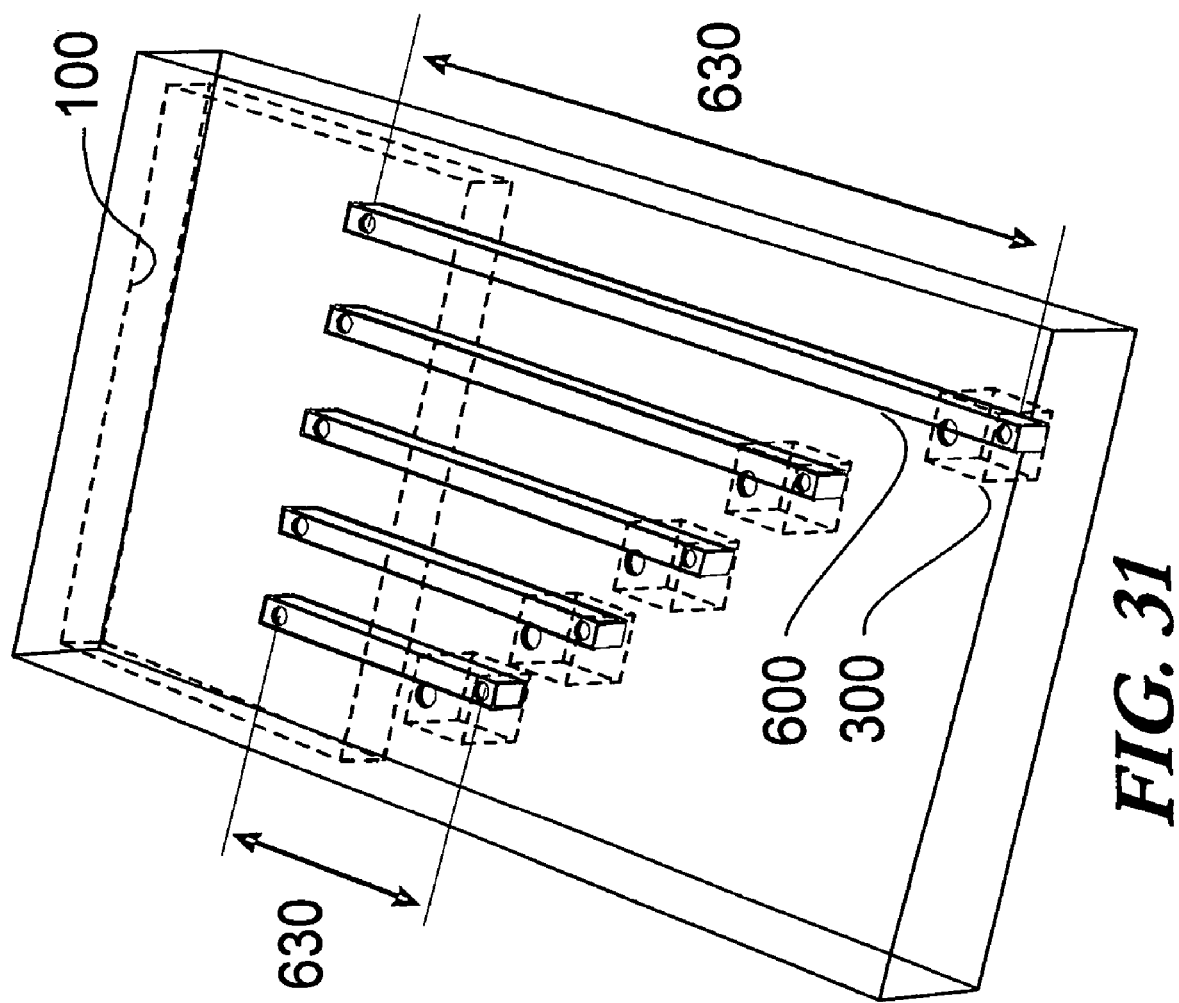
FIG. 31 shows another embodiment of the bioreactor of the instant invention in elevated perspective view, not to scale.

As would be obvious to one skilled in the art, the diffusion controlling bioreactor 50 may be configured to selectively control the molecular diffusion between a first fluid, a second fluid, and a third fluid. Such multiple fluid handling capacity is seen in the embodiments illustrated in FIGS. 12 and 13, which combine the structures illustrated in FIGS. 3, 4, and 7. A second microchannel 600 may be in fluid communication with the reaction reservoir 100. As with the first microchannel 200, the second microchannel 600 has a proximal end 610 with a proximal end opening 612, and a distal end 620 with a distal end opening 622 as seen in FIG. 14. This second microchannel may further include a reagent reservoir 300 at the distal end 620 of the second microchannel 600 in fluid communication with both the second microchannel 600 and the reaction reservoir 100. The reagent reservoir 300 has at least one reagent reservoir sidewall 310 which defines a reagent reservoir volume 320 and a reagent reservoir opening 330 through which the third fluid enters the reagent reservoir 300. The second microchannel 600 has a length 630, and at least one second microchannel sidewall 640 defining a cross-sectional area. The length 630 and cross-sectional area 650 are selected to obtain a predetermined rate of molecular diffusion between the fluid in the second microchannel 600 and the fluid in the reaction reservoir 100. The second microchannel 600 is configured such when the second microchannel 600 is filled with the third fluid, and the third fluid is a liquid, flow of the third fluid through the second microchannel 600 is laminar. The capillary action of the second microchannel 600 and the third fluid is such that the third fluid does not flow into the reaction reservoir 100 unless the pressure of the third fluid is increased by an external source. The instant invention may be configured to have multiple second microchannels and multiple reagent reservoirs, as illustrated in the embodiments seen in FIGS. 26 and 31.

In the nature of capillary flow, surface tension produces a non-flat liquid surface, called a meniscus, at the end of the microchannel 200. If a fluid tends to wet the inside surface of a capillary such as a microchannel 200, as seen in FIG. 27, the meniscus is concave until capillary action draws the fluid to the open end of the capillary, at which point it becomes convex, as seen in FIG. 28.

In the illustrative example of FIG. 28, a convex meniscus forms at the end of the microchannel 200. Should any hydrophilic material touch the meniscus, or should the meniscus contact a fluid of higher solubility and the "interfacial tension" between the first fluid and the second becomes unbalanced in favor of the second, the surface tension of the meniscus will be broken, and fluid will begin to wick through the capillary microchannel 200, thus potentially defeating the instant invention goal of the prevention of fluid movement through the microchannel 200 and thereby defeating the controlled diffusion of the instant invention. As is well-known in the art, a capillary having a very short sidewall will support only a very slightly convex or concave meniscus. Accordingly, creating a section of very thin sidewall 455 at the proximal end opening 212 of the proximal end 210 of the microchannel 200, as seen in FIGS. 29, 30, 39, and 40, will result in an area wherein the capillary effect of the very thin sidewall 455 at the proximal end 212 will be insufficient to support a meniscus, resulting in a relatively flat interface between a fluid in the microchannel 200 and a fluid in the reaction reservoir 100. In various embodiments, thicknesses in this section of sidewall 455 of between about 0.1 mm and 0.5 mm work well to create this effect.

Figure 40:
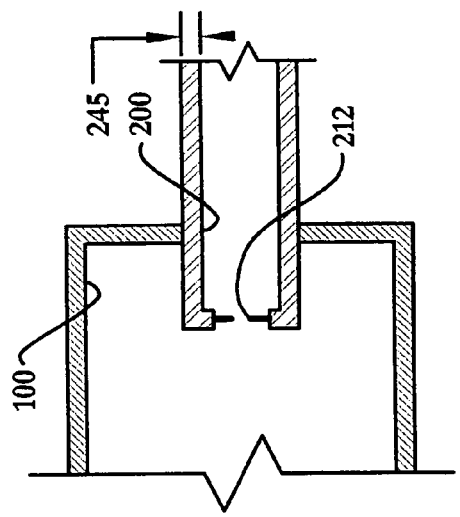
FIG. 40 shows a further embodiment of the sidewall in FIG. 37.

As may be seen, by way of examples and not limitation only, one skilled in the art will realize that the area of very thin sidewall 455 at the proximal end opening 212 of the proximal end 210 of the microchannel 200 may be formed in a wide variety of manners, not limited to the embodiments illustrated. In particular, as seen in FIG. 40, it may be seen that the area of very thin sidewall 240 at the proximal end opening 212 of the proximal end 210 of the microchannel 200 does not represent any particular requirements as to diameter of the proximal end opening 212.

Figure 29:
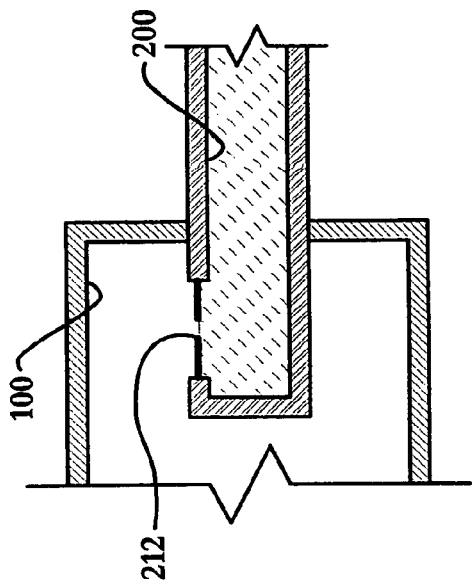
FIG. 29 shows a portion of an embodiment of the bioreactor of the instant invention in cross-sectional view, not to scale.
Figure 30:
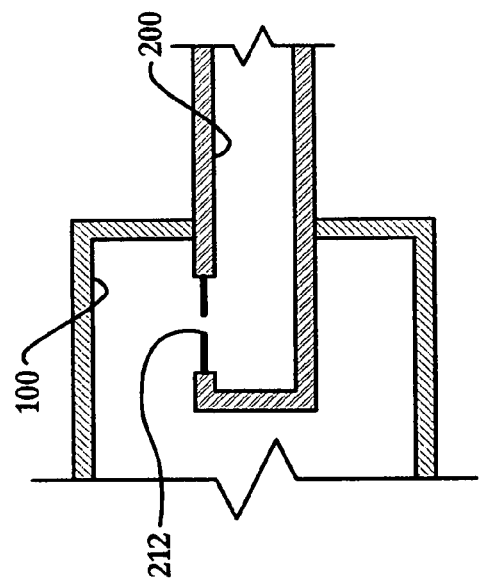
FIG. 30 shows a portion of an embodiment of the bioreactor of the instant invention in cross-sectional view, not to scale.

To serve the same purpose, the same may be true for a second microchannel 600, where the area of the proximal end opening 612 of the second microchannel 600 may be configured to interpose a section of very thin sidewall 640 at the proximal end opening 612 of the proximal end 610 of the second microchannel 600, analogous to such as seen in FIGS. 29 and 30. As with the first microchannel 200, this will result in an area wherein the capillary effect of the very thin sidewall 640 at the proximal end 612 will be insufficient to support a meniscus, resulting in a relatively flat interface between a fluid in the microchannel 600 and a fluid in the reaction reservoir 100.

In yet another embodiment, seen in FIGS. 14 through 18, the diffusion controlling bioreactor 50 may further include a pressure equalizing vent 400 in fluid communication with the reaction reservoir 100 and a fluidic external environment, wherein the pressure equalizing vent 400 is capable of equalizing the pressure within the reaction reservoir 100 with that of the external environment, as shown in FIG. 15. The pressure equalization vent 400 has a vent microchannel 410 with a distal end 420 with a distal end opening 422 in communication with the external environment. The vent microchannel 410 may further have a length 440, at least one sidewall 450, having a sidewall thickness 455, and defining a cross-sectional area 460, and a proximal end 430 with a proximal end opening 432 in communication with the reaction reservoir 100. The pressure equalizing vent 400 is configured such that when it is filled with a third fluid and the third fluid is a liquid; flow of the third fluid through the pressure equalizing vent 400 is laminar, as with the first microchannel 200 and the second microchannel 600. The capillary action of the pressure equalizing vent 400 and the third fluid is such that the third fluid does not flow out of the distal end opening 422 unless the pressure of the third fluid is increased by an external source.

Figure 7:
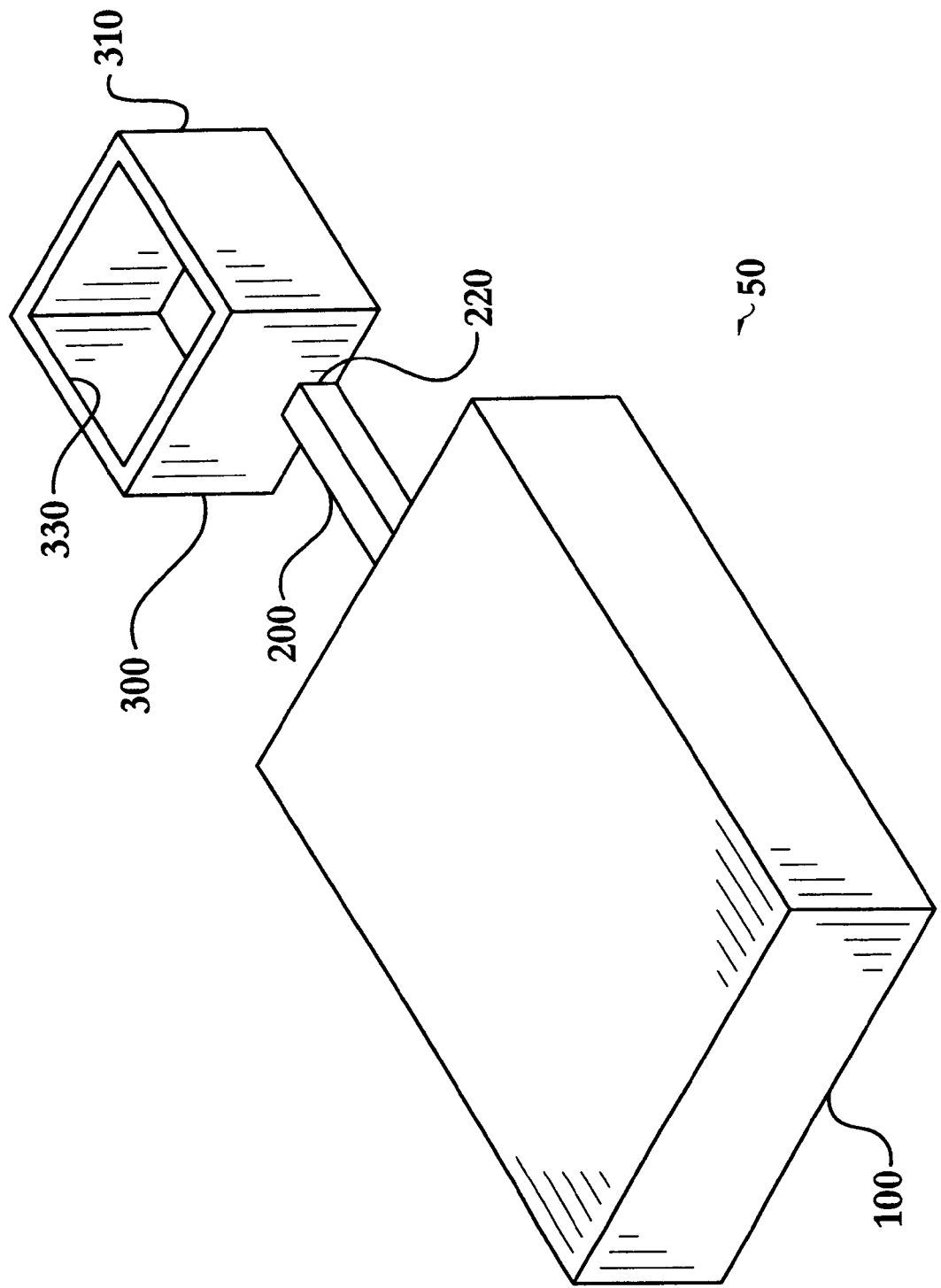
FIG. 7 shows another embodiment of a bioreactor according to the instant invention in elevated perspective view, not to scale.

An illustrative example of such a pressure equalizing vent 400 is seen in FIGS. 14 through 18. The filling of the reaction reservoir 100 with a second fluid results in a third fluid flowing from the reaction reservoir 100 into the vent microchannel 410 through the proximal end opening 432 of the vent microchannel 410. Examination will reveal that the operative principles regulating the transport of molecules through such a pressure equalizing vent 400 are essentially identical to those of the embodiment utilizing a reagent reservoir 300 and a reaction reservoir 100, as seen in FIG. 7, with the exception that in those embodiments utilizing a pressure equalizing vent 400, the vent microchannel 410 connects the reaction reservoir 100 with an external environment, rather than connecting the reagent reservoir 300 with the reaction reservoir 100, as with the first and second microchannels 200, 600. Thus, there may be passage of gas molecules between the external environment and the reaction reservoir 100, subject to the same controlled diffusion principles as discussed above. Again as applied to the instant invention, the formation of a virtual "seal" by the vent microchannel 410, analogous to the virtual "seal" created by the microchannel 200, may be used to limit the diffusion of gases into and out of the bioreactor 50 to that which takes place across the walls of the bioreactor.

The pressure equalizing vent 400 may include, as seen in FIGS. 17 through 18, at the distal end opening 422, a filter 500 that is hydrophobic and capable of substantially preventing, at normal operating pressures, flow of liquid through the filter 500. The filter 500 may further include an assembly, seen in FIG. 18, of at least 2 layers with a first layer 510 being adapted to prevent the passage of particles having an average size of at least approximately 80 microns, and a second layer 520 being adapted to prevent the passage of particles having an average size of at least approximately 0.2 microns. Such a filter 500 serves two functions, the prevention of the ingress of contaminants greater than the effective filtration size of the filter, i.e., those particles greater than at least approximately 0.2 microns; and the prevention of particle and fluid movement through the hydrophobic filter 500 and into the external environment should the reaction reservoir become somewhat pressurized above the pressure in the pressure equalization vent 400.

Figure 37:
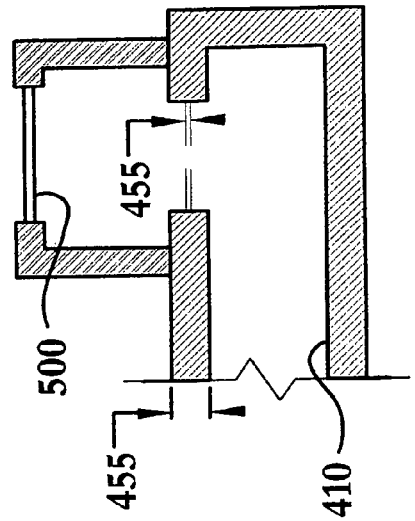
FIG. 37 shows a thin sidewall insufficient to support a meniscus.
Figure 38:
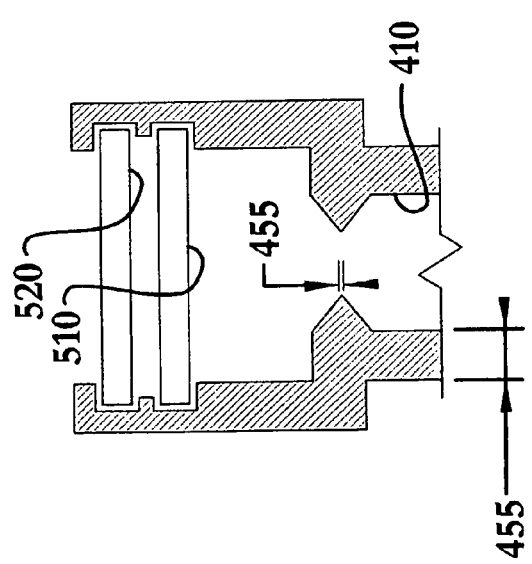
FIG. 38 shows an alternative embodiment of the sidewall in FIG. 37.
Figure 39:
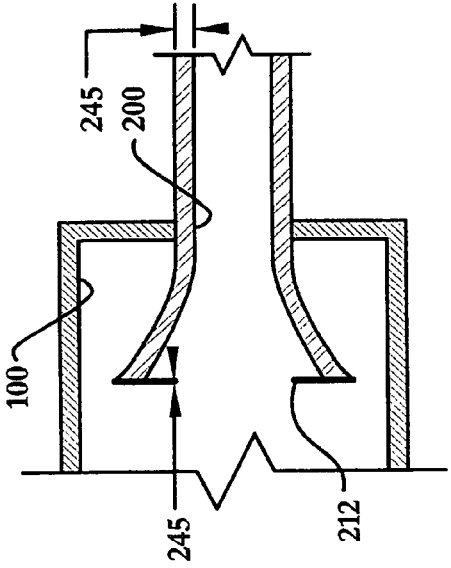
FIG. 39 shows an alternative embodiment of the sidewall in FIG. 37.

A convex meniscus may form at the end of the vent microchannel 400 similar to the meniscus illustrated in FIG. 28, Should this meniscus touch the material of the filter 500, the surface tension of the meniscus will be broken, and fluid will begin to wick through the vent microchannel 410, thus wetting the filter 500 and potentially decreasing the effectiveness of the filter 500. Just as the creation of a section of very thin sidewall 455 at the proximal end opening 212 of the proximal end 210 of the microchannel 200, as seen in FIGS. 29 30, 39, and 40, will result in an area wherein the capillary effect of the very thin sidewall 455 at the proximal end 212 will be insufficient to support a meniscus at the proximal end 212, an analogous structure, seen in FIGS. 37 and 38; an analogous structure at the distal end 420 of the vent microchannel 410 will result in a relatively flat interface between a fluid in the vent microchannel 410 and a fluid, which may be air, between the distal end 420 and the filter 500.

The flatter meniscus is less likely to extend beyond the distal end opening 422 of the vent microchannel 400, and therefore the fluid in the vent microchannel 410 is less likely to contact the filter 500. In various embodiments, thicknesses in this section of sidewall 455 of between about 0.1 mm and 0.5 mm work well to create this effect.

Figure 19:
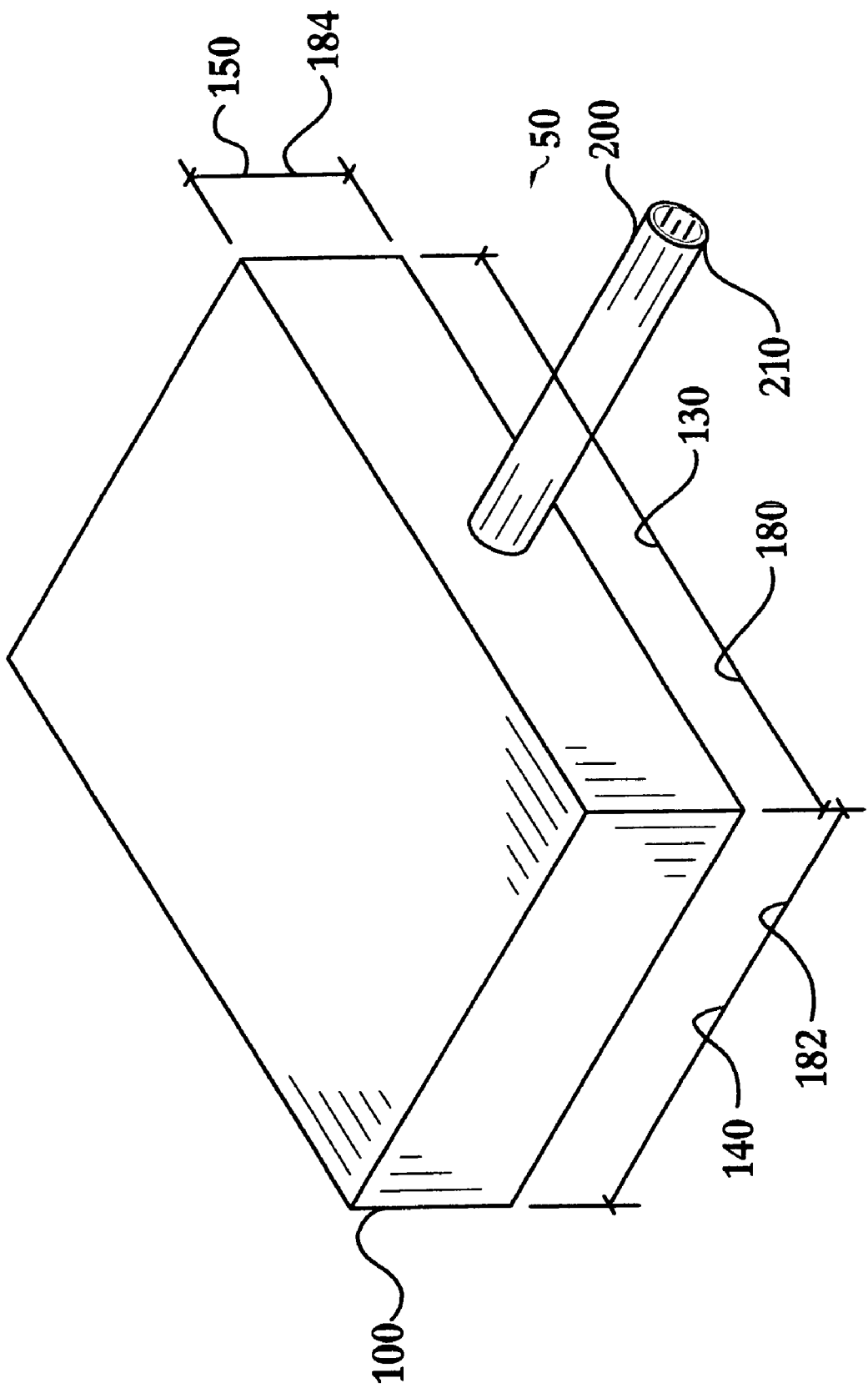
FIG. 19 shows another embodiment of the bioreactor of FIG. 2 in elevated perspective view, not to scale.
Figure 20:
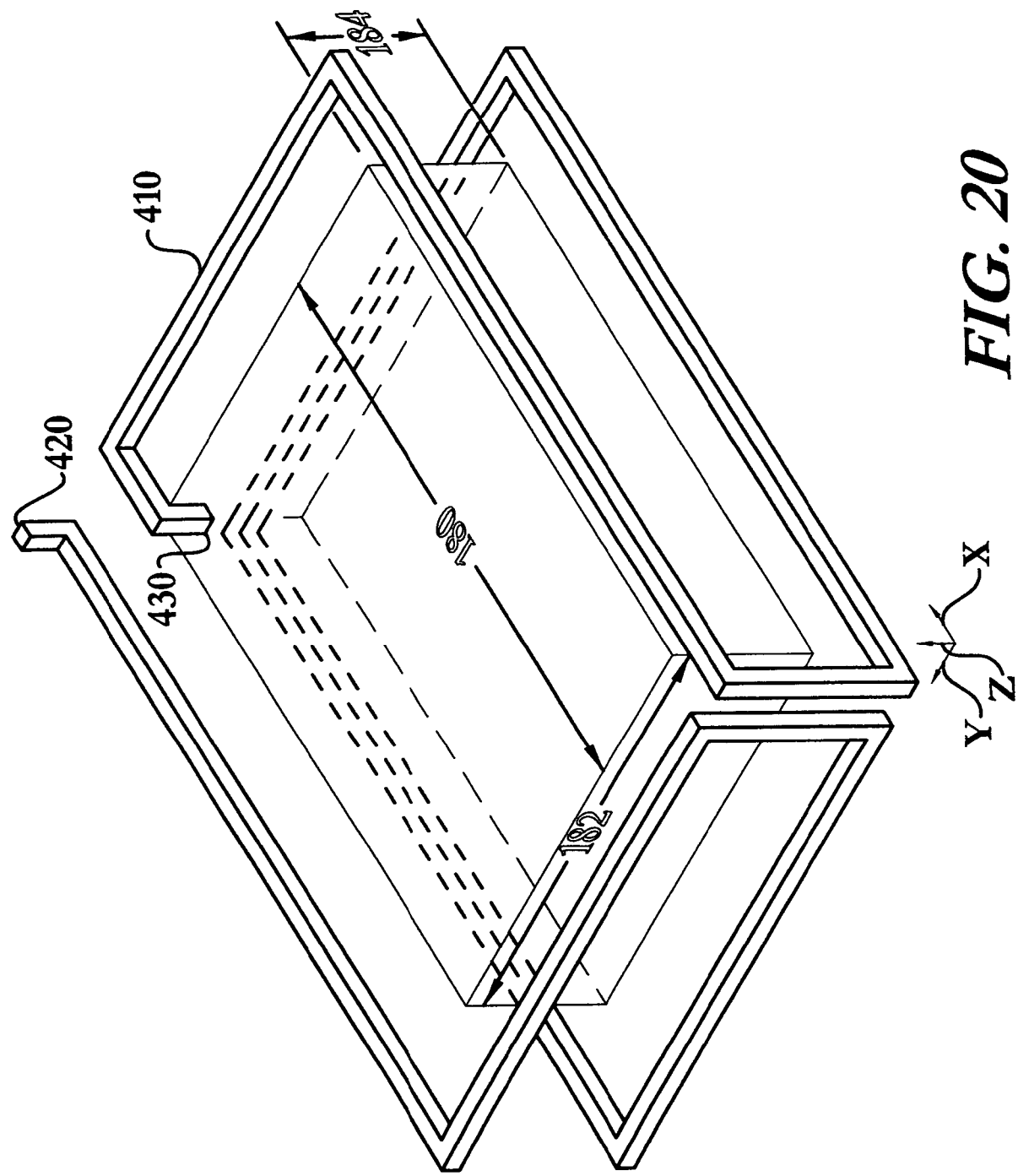
FIG. 20 shows another embodiment of the bioreactor of FIG. 19 in elevated perspective view, not to scale.
Figure 25:
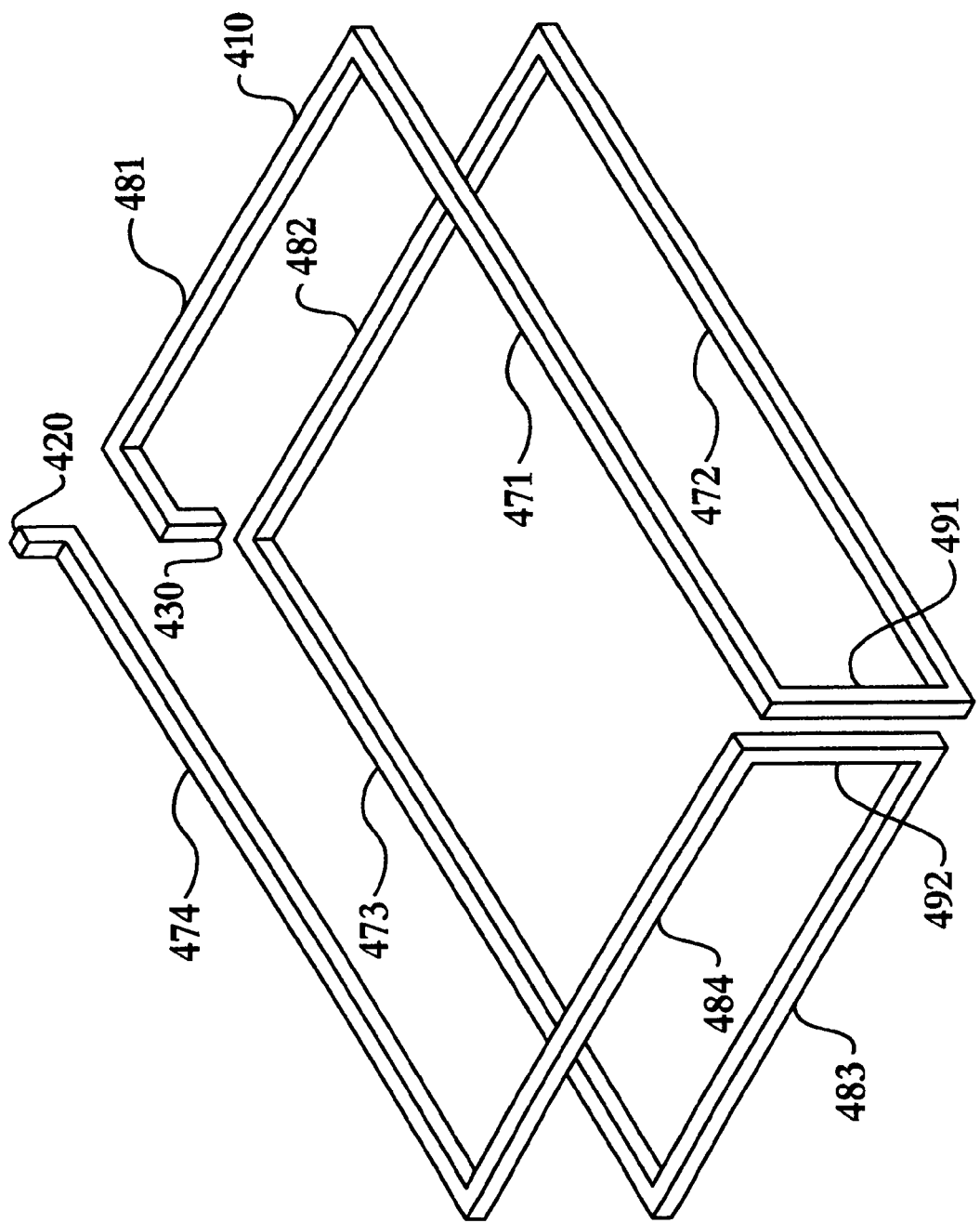
FIG. 25 shows a portion of the embodiment of FIG. 20 of the bioreactor of the instant invention in elevated perspective view, not to scale.

The pressure equalizing vent 400 may have a structure configured to minimize the chances of fluid leakage from the bioreactor 50, seen in FIGS. 20 and 25, even if the bioreactor 50 is turned in various directions. In such an embodiment, the reaction reservoir 100 has a maximum first dimension in a primary axis 130, a maximum second dimension in a secondary axis 140, and a maximum third dimension in a tertiary axis 150, seen in FIG. 19. Further, seen in FIG. 20, in such a design, the pressure equalizing vent 400 includes a continuous vent microchannel 410 configured exterior to the reaction reservoir 100. Such a vent microchannel 410 would include at least one component in the primary axis X with a magnitude greater than the maximum first dimension 130, at least one component in the secondary axis Y with a magnitude greater than the maximum second dimension 140, and at least one component in the tertiary axis Z with a magnitude greater than the maximum third dimension 150, as seen in FIG. 19.

In a preferred embodiment, seen in FIGS. 21 and 24, the reaction reservoir is a hexahedron having a first longitudinal surface 162, a second longitudinal surface 164, a first lateral surface 166, a second lateral surface 168, a top surface 170, and a bottom surface 172, thereby defining a reaction reservoir length 180, width 182, and depth 184, as seen in FIG. 20. In such an embodiment, as seen in FIG. 25, the continuous vent microchannel 410 has four sections 471, 472, 473, 474 substantially parallel to the length 180 and greater in magnitude than the length 180; four sections 481, 482, 483, 484 substantially parallel to the width 182 and greater in magnitude than the width 182; and two sections 491, 492 substantially parallel to the depth 184 and greater in magnitude than the depth 184.

Examination of such an embodiment shows that should the bioreactor 50 be rotated though one or more dimensions of space, the configuration is such that the vent microchannel 410 would include at least one component of the sections in the primary axis X with a magnitude greater than the maximum first dimension 130, at least one component of the sections in the secondary axis Y with a magnitude greater than the maximum second dimension 140, and at least one component of the sections in the tertiary axis Z with a magnitude greater than the maximum third dimension 150. This results in at least a portion of at least one section 471, 472, 474, 474, 481, 482, 483, 484, 491, 492 lying above the fluid level in the bioreactor 50 at all times. As such, during rotation, a significant portion of the fluid in the vent microchannel 410 will drain back into the reaction reservoir 100, while a portion will advance into the adjoining section 471, 472, 474, 474, 481, 482, 483, 484, 491, 492 of the vent microchannel 410. This drain and advance process will be repeated with each turn in any dimension of the bioreactor 50, such that only a concerted effort to rotate the bioreactor 50 through sequential turns in more than one dimension, designed to advance the fluid through the vent microchannel 410, will result in a significant amount of fluid reaching the filter 500.

The tendency for the fluid in one section of the vent microchannel 410 to drain back into the reaction reservoir 100 during rotation of the bioreactor 50 also acts to minimize pressure build up at the distal end opening 422 of the vent microchannel 410 due to a static column of fluid, as the weight of the fluid in a draining section tends to counteract, and thereby pull back, against the weight of any fluid advancing in the vent microchannel 410. The minimization of pressure at the distal end opening 422 of the vent microchannel therefore tends to minimize expulsion of fluid at the distal end opening 422 of the vent microchannel 410, should any fluid reach the distal end opening 422, and thereby to minimize the chances of fluid contamination of the filter 500.

In other preferred embodiments, the bioreactor 50 may be configured with a plurality of reagent reservoirs 300, each at the distal end 620 of a second microchannel 600 that is in fluid communication with both the second microchannel 600 and the reaction reservoir 100. In such an embodiment, each reagent reservoir 300 may be in fluid communication with a second microchannel 600 having different second microchannel lengths 630, and/or cross sectional areas 650 from the other second microchannels 600. This, as seen in illustrative embodiments in FIGS. 26 and 31, enables multiple simultaneous controlled diffusion processes involving different substances to take place coincidentally, but at different rates. Such multiple arrangements of reagent reservoirs 300 in fluid communication through second microchannels 600 to the reaction reservoir 100 is ideal, as would be appreciated by one skilled in the art, for testing or controlling the effects of diffusion of various drugs, nutrients, or other substances, into the process contained in the bioreactor 50. Additionally, the very slow rates of diffusion that may be achieved by the bioreactor 50 of the instant invention make it ideal for the transport of very small quantities of substances into the bioreactor 50 in a very stable and accurate manner over long periods of time.

Figure 32:
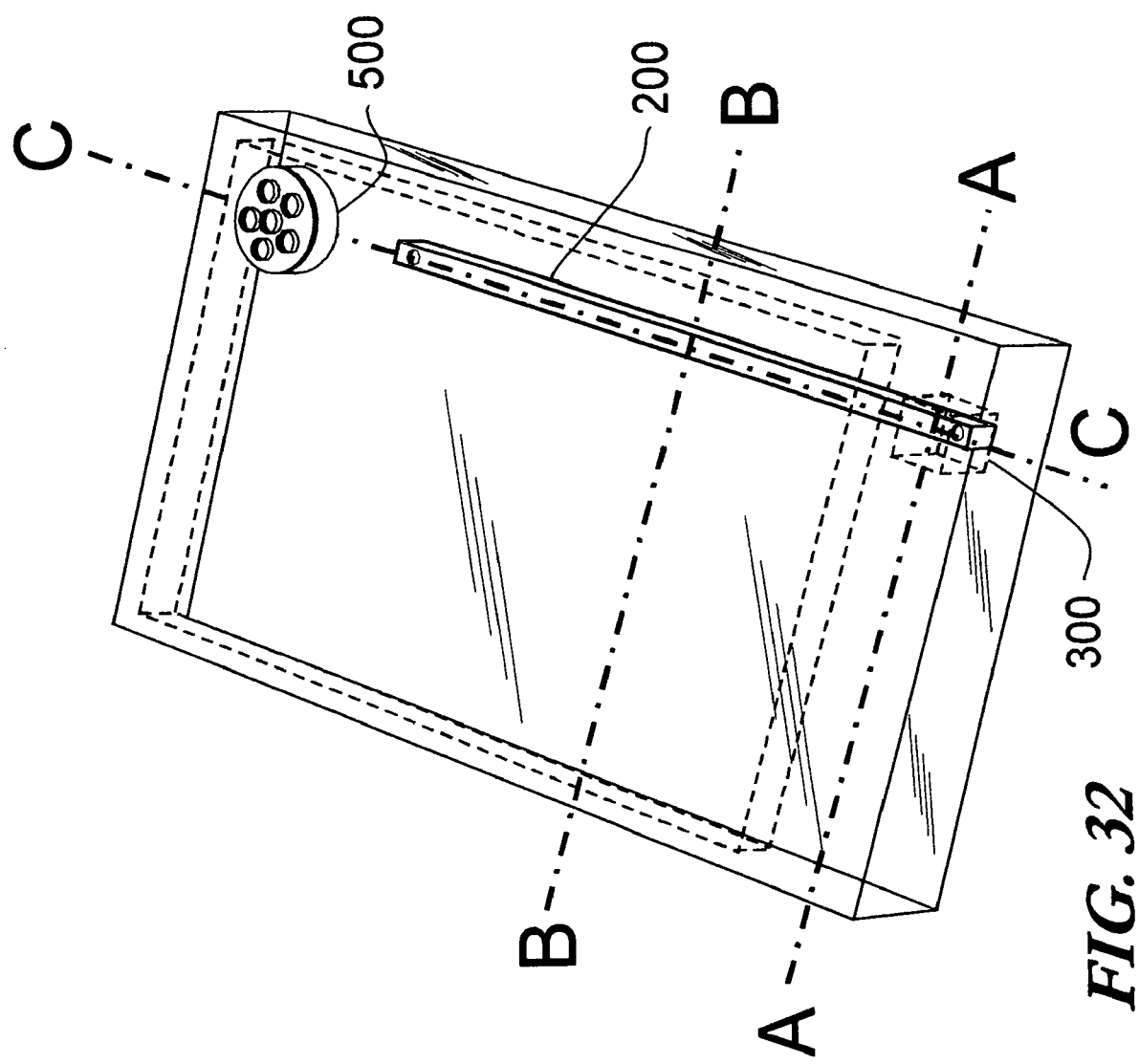
FIG. 32 shows another embodiment of the bioreactor of the instant invention in elevated perspective view, not to scale.

An illustrative embodiment of the instant invention is seen in FIGS. 31-35. In this embodiment, the reaction reservoir 100, first microchannel 200 and filter 500 are formed as part of an integral structure, for strength and ease of handling, as seen in FIG. 32. In FIG. 33, a penetrable elastomeric septum 333 closes the reagent reservoir 300 at the distal end 220 of the microchannel. As seen in FIG. 34, the microchannel 200 runs within the integral structure, and inferior to the reaction reservoir 100. In this particular illustrative embodiment, in which the reaction reservoir 100 may be vented as shown, viewed in cross-section in FIG. 35, the relationship between the reaction reservoir 100, a microchannel 200, and a filter 500 may be visualized.

Numerous alterations, modifications, and variations of the preferred embodiments disclosed herein will be apparent to those skilled in the art and they are all anticipated and contemplated to be within the spirit and scope of the instant invention. For instance, it is understood that the specification of a first fluid, a second fluid, and a third fluid are for illustration, and not limitation, only. The fluids may all be of the same composition, or may be different. Additionally, the illustration of particular features in various embodiments is for illustration, and not limitation, only. Any or all of the various features of the instant invention maybe combined in various illustrated and non-illustrated embodiments, as would be known to one skilled in the art. Further, although specific embodiments have been described in detail, those with skill in the art will understand that the preceding embodiments and variations can be modified to incorporate various types of substitute and or additional or alternative materials, relative arrangement of elements, and dimensional configurations. Accordingly, even though only few variations of the present invention are described herein, it is to be understood that the practice of such additional modifications and variations and the equivalents thereof, are within the spirit and scope of the invention as defined in the following claims. The corresponding structures, materials, acts, and equivalents of all means or step plus function elements in the claims below are intended to include any structure, material, or acts for performing the functions in combination with other claimed elements as specifically claimed.

I claim:

1. A diffusion controlling bioreactor that selectively controls the molecular diffusion between a first fluid and a second fluid, comprising:

a reaction reservoir having at least one reaction reservoir sidewall thereby defining a reaction reservoir volume, wherein the reaction reservoir initially contains the first fluid;

a microchannel having at least one portion fully enclosed by at least one sidewall, in fluid communication with the reaction reservoir, having a proximal end with a proximal end opening, a distal end with a distal end opening, a length, the at least one microchannel sidewall defining a cross-sectional area, wherein the length and cross-sectional area are selected to obtain a predetermined rate of molecular diffusion between the first fluid and the second fluid, and wherein the microchannel is configured such when the microchannel is filled with the second fluid, and the second fluid is a liquid, that flow of the second fluid through the microchannel is laminar and the capillary action of the microchannel and the second fluid is such that the second fluid does not flow into the reaction reservoir unless the pressure of the second fluid is increased by an external source; and a pressure equalizing vent in fluid communication with the reaction reservoir and a fluidic external environment, wherein the pressure equalizing vent is capable of equalizing pressure within the reaction reservoir with that of the external environment, wherein the pressure equalization vent has a distal end with a distal end opening in communication with the external environment, a length, at least one sidewall, having a sidewall thickness, and defining a cross-sectional area, and a proximal end with a proximal end opening in communication with the reaction reservoir, and wherein the pressure equalizing vent is configured such that when it is filled with a third fluid, and the third fluid is a liquid, that flow of the third fluid through the pressure equalizing vent is laminar and the capillary action of the pressure equalizing vent and the third fluid is such that the third fluid does not flow out of the distal end opening unless the pressure of the third fluid is increased by an external source;

wherein the reaction reservoir has a maximum first dimension in a primary axis, a maximum second dimension in a secondary axis, and a maximum third dimension in a tertiary axis, and the pressure equalizing vent is a continuous microchannel configured lying wholly exterior to the reaction reservoir and having at least one component in the primary axis with a magnitude greater than the maximum first dimension, at least one component in the secondary axis with a magnitude greater than the maximum second dimension, and at least one component in the tertiary axis with a magnitude greater than the maximum third dimension.

2. The bioreactor of claim 1, wherein the distal end opening is closed by a penetrable, elastomeric, self-sealing septum covering the distal end opening.

3. The bioreactor of claim 1, further including a reagent reservoir at the distal end of the microchannel and in fluid communication with both the microchannel and the reaction reservoir, wherein the reagent reservoir has at least one reagent reservoir sidewall thereby defining a reagent reservoir volume and a reagent reservoir opening through which the second fluid enters the reagent reservoir.

4. The bioreactor of claim 3, wherein the reagent reservoir opening is closed by a penetrable, self-sealing, elastomeric septum covering the reagent reservoir opening.

5. The bioreactor of claim 1, wherein the proximal end opening further includes a section of the microchannel sidewall configured to have a reduced thickness sufficient to minimize formation of a meniscus at the proximal end opening by a fluid within the microchannel.

6. The bioreactor of claim 3, wherein the proximal end opening blocks the flow of liquid in the microchannel when the pressure of the liquid is not increased by an external source and there is a difference in viscosity between the first fluid and the second fluid, while permitting the diffusion of molecules across the proximal end opening.

7. The bioreactor of claim 1, wherein the cross-sectional area of the microchannel is less than 4 mm$^2$.

8. The bioreactor of claim 1, wherein the length of the microchannel is equal to or between 1 cm and 10 cm.

9. The bioreactor of claim 1, wherein the distal end opening of the pressure equalizing vent further includes a filter that is hydrophobic and capable of substantially preventing flow of liquid through the filter.

10. The bioreactor of claim 9, wherein the filter further includes an assembly of at least 2 layers with a first layer being adapted to prevent the passage of particles having an average size of at least approximately 80 microns, and a second layer being adapted to prevent the passage of particles having an average size of at least approximately 0.2 microns.

11. The bioreactor of claim 1, wherein the area of the distal end opening of the pressure equalizing vent further includes a section of the vent sidewall configured to have a reduced thickness sufficient to minimize formation of a meniscus at the proximal end opening by a fluid within the vent.

12. The bioreactor of claim 11, wherein the distal end opening of the pressure equalizing vent blocks the flow of liquid in the pressure equalizing vent when the pressure of the liquid is not increased by an external source and there is a difference in viscosity between the third fluid and the external environment, while permitting the diffusion of molecules across the distal end opening.

13. The bioreactor of claim 1, wherein the reaction reservoir is a hexahedron having a first longitudinal surface, a second longitudinal surface, a first lateral surface, a second lateral surface, a top surface, and a bottom surface, thereby defining a reaction reservoir length, width, and depth, and wherein the continuous microchannel has four sections substantially parallel to the length and greater in magnitude, four sections substantially parallel to the width and greater in magnitude, and two sections substantially parallel to the depth and greater in magnitude.

14. A diffusion controlling bioreactor that selectively controls the molecular diffusion between a first fluid, a second fluid, and a third fluid, comprising:

a reaction reservoir having at least one reaction reservoir sidewall thereby defining a reaction reservoir volume, wherein the reaction reservoir initially contains the first fluid;

a microchannel having at least one portion fully enclosed by at least one sidewall, in fluid communication with the reaction reservoir, having a proximal end with a proximal end opening, a distal end with a distal end opening, a length, the at least one microchannel sidewall defining a cross-sectional area, wherein the length and cross-sectional area are selected to obtain a predetermined rate of molecular diffusion between the first fluid and the second fluid, and wherein the microchannel is configured such when the microchannel is filled with the second fluid, and the second fluid is a liquid, that flow of the second fluid through the microchannel is laminar and the capillary action of the microchannel and the second fluid is such that the second fluid does not flow into the reaction reservoir unless the pressure of the second fluid is increased by an external source; and a pressure equalizing vent in fluid communication with the reaction reservoir and a fluidic external environment, wherein the pressure equalizing vent is capable of equalizing pressure within the reaction reservoir with that of the external environment, wherein the pressure equalization vent has a distal end with a distal end opening in communication with the external environment, a length, at least one sidewall, having a sidewall thickness, and defining a cross-sectional area, and a proximal end with a proximal end opening in communication with the reaction reservoir, and wherein the pressure equalizing vent is configured such that when it is filled with a third fluid, and the third fluid is a liquid, that flow of the third fluid through the pressure equalizing vent is laminar and the capillary action of the pressure equalizing vent and the third fluid is such that the third fluid does not flow out of the distal end opening unless the pressure of the third fluid is increased by an external source; and wherein the area of the distal end opening of the pressure equalizing vent includes a section of the vent sidewall configured to have a reduced thickness sufficient to minimize formation of a meniscus at the proximal end opening by a fluid within the vent.

15. The bioreactor of claim 14, further including a reagent reservoir at the distal end of the microchannel and in fluid communication with both the microchannel and the reaction reservoir, wherein the reagent reservoir has at least one reagent reservoir sidewall thereby defining reagent reservoir volume and a reagent reservoir opening through which the second fluid enters the reagent reservoir.

16. The bioreactor of claim 15, wherein the reagent reservoir opening is closed by a penetrable, self-sealing, elastomeric septum covering the reagent reservoir opening.

17. The bioreactor of claim 14, wherein the proximal end opening further includes a section of the microchannel sidewall configured to have a reduced thickness sufficient to minimize formation of a meniscus at the proximal end opening by a fluid within the microchannel.

18. The bioreactor of claim 17, wherein the microchannel proximal end opening blocks the flow of liquid in the microchannel when the pressure of the liquid is not increased by an external source and there is a difference in viscosity between the first fluid and the second fluid, while permitting the diffusion of molecules across the microchannel proximal end opening.

19. The bioreactor of claim 14, wherein the cross-sectional area of the microchannel is less than 4 mm$^2$.

20. The bioreactor of claim 14, wherein the length of the microchannel is equal to or between 1 cm and 10 cm.

21. The bioreactor of claim 14, wherein the vent distal end opening further includes a filter that is hydrophobic and capable of preventing flow of liquid through the filter.

22. The bioreactor of claim 21, wherein the filter further includes an assembly of at least 2 layers with a first layer being adapted to prevent the passage of particles having an average size of at least approximately 80 microns, and a second layer being adapted to prevent the passage of particles having an average size of at least approximately 0.1 microns.

23. The bioreactor of claim 14, wherein the distal end opening of the pressure equalizing vent blocks the flow of liquid in the pressure equalizing vent when the pressure of the liquid is not increased by an external source and there is a difference in viscosity between the third fluid and the external environment, while permitting the diffusion of molecules across the vent distal end opening.

24. The bioreactor of claim 14, wherein the reaction reservoir has a maximum first dimension in a primary axis, a maximum second dimension in a secondary axis, and a maximum third dimension in a tertiary axis, and the pressure equalizing vent is a continuous microchannel configured lying wholly exterior to the reaction reservoir and having at least one component in the primary axis with a magnitude greater than the maximum first dimension, at least one component in the secondary axis with a magnitude greater than the maximum second dimension, and at least third component in the tertiary axis with a magnitude greater than the maximum third dimension.

25. The bioreactor of claim 14, wherein the reaction reservoir is a hexahedron having a first longitudinal surface, a second longitudinal surface, a first lateral surface, a second lateral surface, a top surface, and a bottom surface, thereby defining a reaction reservoir length, width, and depth, and wherein the continuous microchannel has four sections substantially parallel to the length and greater in magnitude, four sections substantially parallel to the width and greater in magnitude, and two sections substantially parallel to the depth and greater in magnitude.

26. A diffusion controlling bioreactor that selectively controls the molecular diffusion between a first fluid, a second fluid, and a third fluid, comprising:
　a reaction reservoir having at least one reaction reservoir sidewall thereby defining a reaction reservoir volume, wherein the reaction reservoir initially contains the first fluid;
　a first microchannel having at least one portion fully enclosed by at least one sidewall, in fluid communication with the reaction reservoir, having a proximal end with a proximal end opening, a distal end with a distal end opening, a length, the at least one microchannel sidewall defining a cross-sectional area, wherein the length and cross-sectional area are selected to obtain a predetermined rate of molecular diffusion between the first fluid and the second fluid, and wherein the first microchannel is configured such when the first microchannel is filled with the second fluid, and the second fluid is a liquid, that flow of the second fluid through the first microchannel is laminar and the capillary action of the first microchannel and the second fluid is such that the second fluid does not flow into the reaction reservoir unless the pressure of the second fluid is increased by an external source, and wherein the proximal end opening of the first microchannel includes a section of the first microchannel sidewall configured to have a reduced thickness sufficient to minimize formation of a meniscus at the proximal end opening by a fluid within the first microchannel; and
　a second microchannel in fluid communication with the reaction reservoir, having a proximal end with a proximal end opening, a distal end with a distal end opening, further including a reagent reservoir at the distal end of the second microchannel and in fluid communication with both the second microchannel and the reaction reservoir, wherein the reagent reservoir has at least one reagent reservoir sidewall thereby defining reagent reservoir volume and a reagent reservoir opening through which the third fluid enters the reagent reservoir, a length, at least one second microchannel sidewall, having a sidewall thickness, and defining a cross-sectional area, wherein the length and cross-sectional area are selected to obtain a predetermined rate of molecular diffusion between the first fluid and the third fluid, and wherein the second microchannel is configured such when the second microchannel is filled with the third fluid, and the third fluid is a liquid, that flow of the third fluid through the second microchannel is laminar and the capillary action of the second microchannel and the third fluid is such that the third fluid does not flow into the reaction reservoir unless the pressure of the third fluid is increased by an external source; and
　wherein the proximal end opening of the first microchannel blocks the flow of liquid in the first microchannel when the pressure of the liquid is not increased by an external source and there is a difference in viscosity between the first fluid and the second fluid, while permitting the diffusion of molecules across the proximal end opening of the first microchannel.

27. The bioreactor of claim 26, wherein the reagent reservoir opening is closed by a penetrable, self-sealing, elastomeric septum covering the reagent reservoir opening.

28. The bioreactor of claim 26, wherein the proximal end opening of the second microchannel further includes a section of the second microchannel sidewall configured to have a reduced thickness sufficient to minimize formation of a meniscus at the proximal end opening by a fluid within the second microchannel.

29. The bioreactor of claim 26, wherein the proximal end opening of the second microchannel blocks the flow of liquid in the second microchannel when the pressure of the liquid is not increased by an external source and there is a difference in viscosity between the first fluid and the second fluid, while permitting the diffusion of molecules across the proximal end opening of the second microchannel.

30. The bioreactor of claim 26, wherein the length and cross-sectional area of the second microchannel are selected to achieve a predetermined rate of diffusion between the third fluid and the first fluid.

31. The bioreactor of claim 26, wherein the reaction reservoir is constructed of a material having a diffusion capacity and with sidewalls having a surface area such that the diffusion of oxygen across the sidewalls is predetermined for a predetermined unit of time.

32. The bioreactor of claim 31 wherein the oxygen diffusion across the reaction reservoir sidewalls is approximately 4.6 ml per day at atmospheric pressure and a temperature of 37° C.

* * * * *